US008036768B2

(12) United States Patent  
Lowe

(10) Patent No.: US 8,036,768 B2
(45) Date of Patent: *Oct. 11, 2011

(54) SYSTEM AND METHOD FOR CREATING ORTHOTICS

(75) Inventor: Craig E. Lowe, Tustin, CA (US)

(73) Assignee: Craig Lowe, Tustin, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 11/877,366

(22) Filed: Oct. 23, 2007

(65) Prior Publication Data

US 2008/0086907 A1    Apr. 17, 2008

Related U.S. Application Data

(63) Continuation of application No. 11/076,580, filed on Mar. 8, 2005, now Pat. No. 7,346,418.

(60) Provisional application No. 60/551,504, filed on Mar. 8, 2004.

(51) Int. Cl.
*G06F 19/00* (2006.01)
*A61B 5/107* (2006.01)

(52) U.S. Cl. ........ 700/118; 702/139; 702/168; 702/166; 600/592; 36/73; 12/146 M

(58) Field of Classification Search .................. 700/118, 700/95; 702/127, 139, 155, 159, 168, 166; 600/592; 36/43; 12/146 M
See application file for complete search history.

(56) References Cited

U.S. PATENT DOCUMENTS 5,339,252 A    8/1994    White et al.
(Continued)

FOREIGN PATENT DOCUMENTS

WO    WO 94/23605    * 10/1994

OTHER PUBLICATIONS

International Search Report for Application No. PCT/US2005/07756, filed Mar. 8, 2005, report completed Jun. 21, 2006, report mailed Dec. 15, 2006, 3 pgs.

(Continued)

*Primary Examiner* — Albert Decady
*Assistant Examiner* — Steven Garland
(74) *Attorney, Agent, or Firm* — Klein, O'Neill & Singh, LLP

(57) ABSTRACT

Systems and methods for constructing custom orthotics are described. Several embodiments of the system use sensor pads to obtain both static and dynamic three dimensional information concerning the shape or topography of the bottom surface of a patient's foot. The information is analyzed to obtain information useful in constructing a custom orthotic from a selection of basic orthotic shells. Once constructed, the orthotic can modify a patient's gait. One embodiment of the present invention includes a user terminal including a sensor pad connected to a computer, a server configured to analyze three dimensional information acquired by the sensor pad, a manufacturing terminal configured to display the results of the server's analysis of the three dimensional information and a network that connects the user terminal to the server and the server to the manufacturing terminal.

19 Claims, 21 Drawing Sheets

U.S. PATENT DOCUMENTS

| | | | |
|---|---|---|---|
| 5,822,223 A | 10/1998 | Genest | |
| 5,925,000 A * | 7/1999 | Marciniak et al. | 600/592 |
| 6,006,412 A * | 12/1999 | Bergmann et al. | 29/407.04 |
| 6,160,264 A | 12/2000 | Rebiere | |
| 6,331,893 B1 | 12/2001 | Brown et al. | |
| 6,804,571 B2 | 10/2004 | Fullen et al. | |
| 6,847,915 B2 | 1/2005 | Liang et al. | |
| 7,346,418 B2 * | 3/2008 | Lowe | 700/118 |
| 2002/0158358 A1 | 10/2002 | Franzene | |
| 2003/0110095 A1 | 6/2003 | Danenberg | |
| 2004/0133431 A1 * | 7/2004 | Udiljak et al. | 705/1 |
| 2004/0143452 A1 * | 7/2004 | Pattillo et al. | 705/1 |
| 2004/0194348 A1 * | 10/2004 | Campbell et al. | 36/93 |
| 2005/0061332 A1 | 3/2005 | Greenawalt et al. | |
| 2005/0171456 A1 | 8/2005 | Hirschman et al. | |

OTHER PUBLICATIONS

Written Opinion for Application No. PCT/US2005/07756, filed Mar. 8, 2005, report completed Jun. 21, 2006, report mailed Dec. 15, 2006, 3 pgs.

* cited by examiner

SYSTEM AND METHOD FOR CREATING ORTHOTICS

CROSS-REFERENCE TO RELATED APPLICATION(S)

This is a Continuation application of Ser. No. 11/076,580, filed Mar. 8, 2005, now U.S. Pat. No. 7,346,418 which claims benefit of Provisional Application No. 60/551,504 filed Mar. 8, 2004 the contents of which are expressly incorporated herein by reference as if set forth in full.

BACKGROUND

The present invention relates generally to the field of information capture and more particularly to the capture of the three dimensional shape of a human foot and the use of captured three dimensional shape information to produce orthotics.

Orthotics are shoe inserts that are intended to correct an abnormal or irregular walking pattern. Orthotics perform functions that make standing, walking and running more comfortable and efficient by altering slightly the angles at which the foot strikes a surface. Orthotics take various forms and are constructed from various materials. Orthotics are generally concerned with improving foot function and minimizing stress forces that could ultimately cause foot deformity and pain.

A rigid orthotic is an orthotic designed to control foot function and can be made of a firm material such as plastic or carbon fiber. Rigid orthotics are often designed to control motion in two major foot joints, which lie directly below the ankle joint. This type of orthotic is commonly recommended by physicians in response to strains, aches and pains in the legs, thighs, and lower back. Rigid orthotics are generally fabricated from a plaster of paris mold of an individual foot. The finished orthotic normally extends along the sole of the heel to the ball or toes of the foot.

Soft orthotics can be used to absorb shock, increase balance and relieve pressure from sore spots. Soft orthotics are typically constructed from soft, compressible materials and may be molded by the action of the foot in walking or fashioned over a plaster impression of the foot. A useful aspect of soft orthotics is that they may be easily adjusted to changing weight-bearing forces. However, material wear can require that they be frequently replaced. Use of soft orthotics has been shown to be effective for treating arthritis suffers, people with foot deformities and patients suffering from diabetic foot. Soft orthotics are typically worn against the sole of the foot and extend from the heel past the ball of the foot to include the toes.

Semirigid orthotics provide for dynamic balance of the foot while walking or participating in sports. When used for participating in sports, the nature of the sport can impact upon the orthotic design. The purpose of a semirigid orthotic is to help guide the foot through proper functions, allowing the muscles and tendons to perform more efficiently. A basic semirigid orthotic can be constructed from layers of soft material that are reinforced with more rigid materials.

Orthotics have typically been constructed by using casting materials to take a mold of the subject's foot. The mold is then used to construct an orthotic that conforms to the base of the subject's foot. Various other orthotics may be used for multidirectional sports or edge-control sports by casting the foot within the shoe, such as a ski boot, ice skate boot, or inline skate boot.

SUMMARY OF THE INVENTION

Embodiments of the present invention can include a user terminal with a sensor pad that is configured to acquire three dimensional information concerning the shape of a patient's foot. The three dimensional information can be provided to a server that analyzes the information and the analyzed information can be provided to a manufacturing terminal, where a technician can use the information to select and shape an orthotic shell. Alternatively, the information can enable the automated manufacture of a custom orthotic. In one aspect of the invention, custom orthotics can be constructed that modify the gait of a patient.

One embodiment of the present invention includes a user terminal including a sensor pad connected to a computer, a server configured to analyze three dimensional information acquired by the sensor pad, a manufacturing terminal configured to display the results of the server's analysis of the three dimensional information and a network that connects the user terminal to the server and the server to the manufacturing terminal.

In another embodiment, the server is configured to determine a center of balance from the three dimensional information.

In a further embodiment, the server is configured to determine a gait line from the three dimensional information.

In yet another embodiment, the server is configured to determine an arch height from the three dimensional information.

In a still further embodiment, the three dimensional information includes a single array of data describing the topography of a bottom surface of a patient's foot.

In another embodiment again, the three dimensional information includes a plurality of arrays of data describing the topography of the portions of a patient's foot contacting the footpad during dynamic motion. In a still further embodiment again, the server uses the plurality of arrays to identify the time spent in the contact, midstance and propulsive phases of a gait cycle.

An embodiment of the method of the invention includes acquiring three dimensional information concerning the shape of a patient's foot, analyzing the three dimensional information and displaying the three dimensional information and the analysis.

In a further embodiment of the method of the invention, the three dimensional information includes information acquired while the patient is stationary and information acquired while the patient is walking.

In another embodiment of the method of the invention, the analysis obtains information concerning the patient's center of balance.

In a still further embodiment of the method of the invention, the analysis obtains information concerning the patient's gait line.

In yet another embodiment of the method of the invention, the analysis obtains information concerning the patient's arch.

In a still further embodiment again of the method of the invention, the analysis obtains the proportion of time spent in the contact, midstance and propulsive phases of a gate cycle.

In yet another embodiment again of the method of the invention, the display is in the form of a printed information sheet.

In a still further additional embodiment, the display is in the form of a graphical display on a computer screen.

In a yet another additional embodiment, the three dimensional information can be displayed in a plurality of different ways.

DETAILED DESCRIPTION OF THE INVENTION

Turning now to the drawings, a system for obtaining information useful in the manufacture of orthotics is illustrated. One aspect of the invention involves a network for collecting three dimensional information concerning the shape of a patient's foot and transmitting the information to a manufacturing facility. The patient information can be collected using footpads, then processed and transmitted over telephone lines or the internet. A manufacturing facility can receive the transmitted information and the information used to generate an orthotic.

Figure 1:
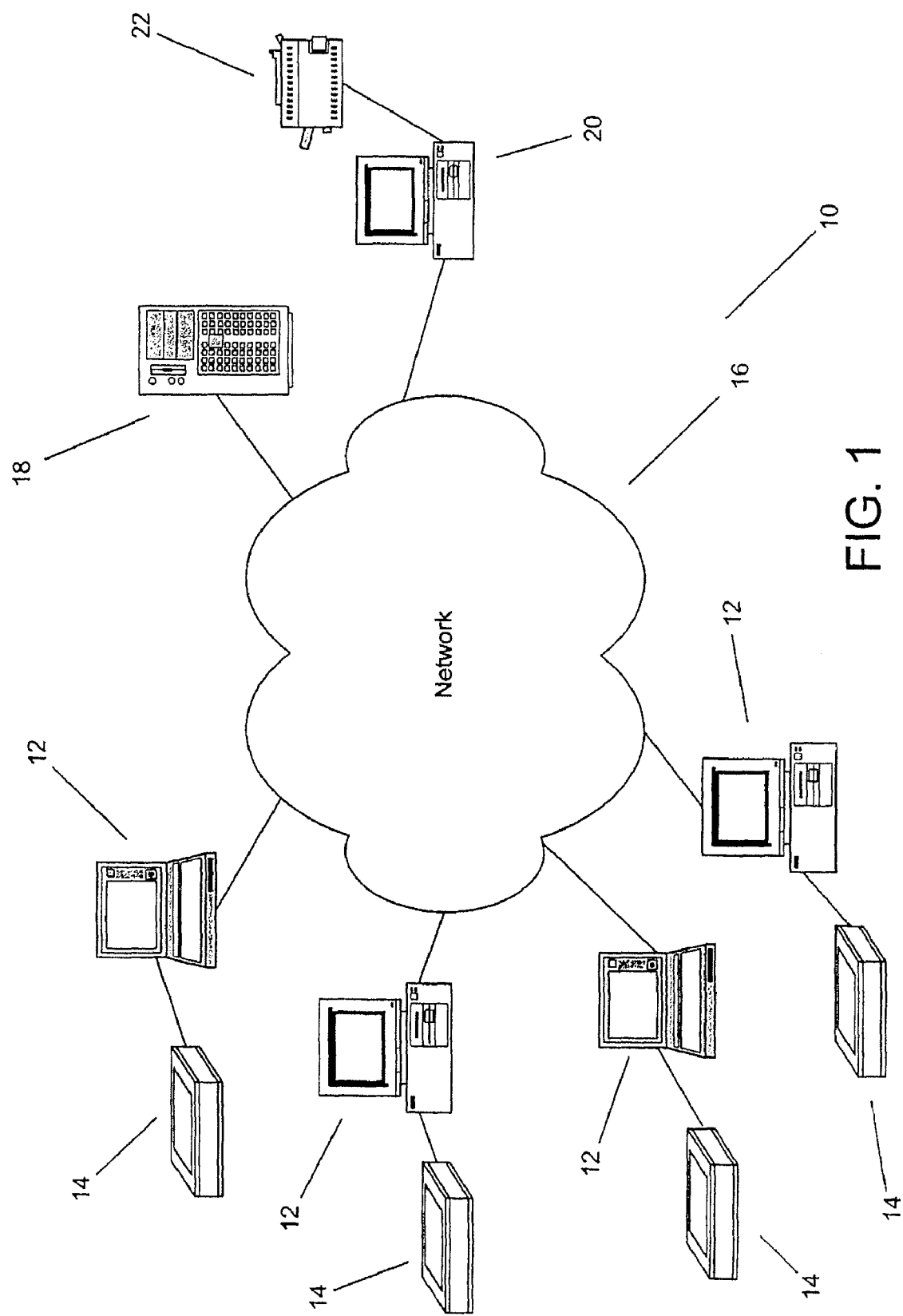
FIG. 1 is a schematic diagram of a network in accordance with an embodiment of the present invention.

A system in accordance with an embodiment of the present invention for collecting three dimensional information concerning the shape of a patient's foot and using the information to manufacture orthotics is illustrated in FIG. 1. The system 10 includes a number of user terminals 12 that include footpads 14. The user terminals are connected to a network 16. A manufacturing terminal is also connected to the network 16.

The user terminals collect information about a patient's foot using the footpads. The information is processed at the user terminal and then sent to the server via the network. The server receives, processes and stores the information and then provides the information to the manufacturing terminal. A lab technician can use the manufacturing terminal to determine the appropriate construction of an orthotic.

Figure 2:
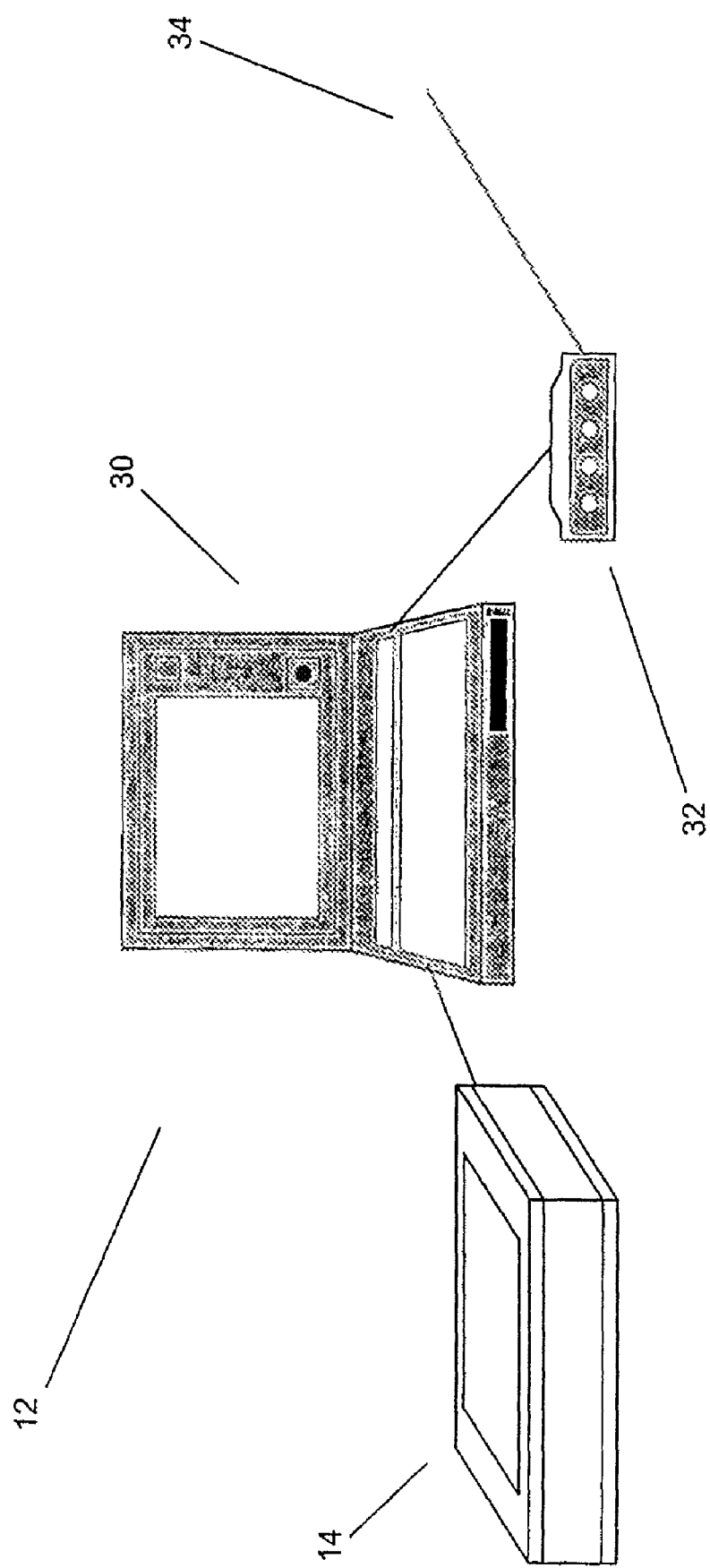
FIG. 2 is a schematic diagram of a user terminal in accordance with an embodiment of the present invention.

A user terminal in accordance with an embodiment of the present invention is illustrated in FIG. 2. The user terminal 12 includes a computer 30. The computer is connected to a footpad 14 and a modem 32. The modem is connected to a telephone line 34. In one embodiment, the user terminal is a self activated kiosk in a retail outlet. In another embodiment, the user terminal is a station located in a doctor's office. Stations located in doctor's offices may contain some of the functionality attributed to other components of the system in accordance with the present invention such as the server and/or the manufacturing terminal (see discussion below).

In several embodiments, the terminal captures three dimensional information concerning the shape of the patient's foot using the footpad. The captured information can then be displayed on the terminal or transferred to another computer over a telephone line using the modem. In other embodiments, the terminal is connected to a network via a network interface card, cable modem or similar network interface device.

Figure 3:
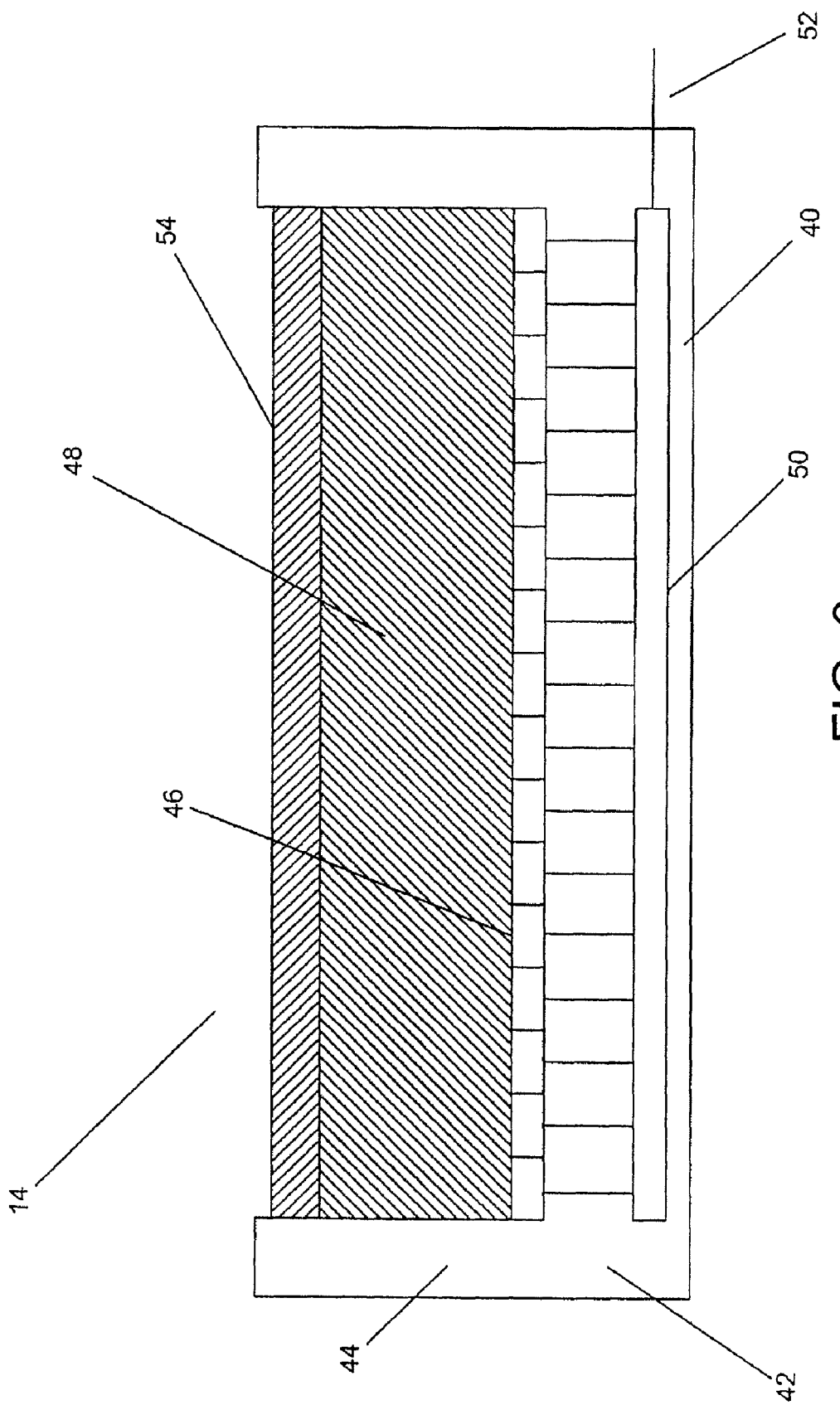
FIG. 3 is a schematic cross-sectional diagram of a footpad in accordance with an embodiment of the present invention.

A footpad in accordance with an embodiment of the present invention is illustrated in FIG. 3. The footpad is a sensor pad that includes a frame 40 that possesses a base 42 and a series of sidewalls 44 that form a tray. An array of electrode cells 46 are located on the bottom surface of the tray formed by the base and the sidewalls. The array of cells are covered by a layer of conductive foam 48 and each electrode cell is connected to an analog-to-digital converter 50. The analog-to-digital converter has an output 52. The conductive foam is covered by a layer of non-conductive material 54.

In one embodiment, the cells are square 24 karat gold plated electrodes that have a side length of 1 cm and the conductive foam is an electroconductive urethane foam. Any flexible and wear resistant non-conductive material can be used to construct the layer of non-conductive material. In several embodiments, 1700 cells are used to form a 18.5 inch by 12 inch sensing area. In addition, the layer of conductive foam has a thickness of 1 inch.

In other embodiments, other metals or piezoelectric materials can be used to construct the electrode cells. In other embodiments, other eletroconductive foams can be used to construct the layer of conductive foam. In addition, a greater or lesser number of cells can be used to create footpads having larger or smaller sensing areas and/or higher or lower resolution.

In operation, patients places one or both of their feet on the layer of non-conductive material and the feet compress the foam. A localized electrical discharge occurs throughout the foam that is dependent upon the amount of compression caused by a patient's foot. The localized discharge is detected by an adjacent electrode cell. Measurements of the current in each of the electrodes can be indicative of the extent to which the base of the patient's foot has compressed the foam in the region above each of the electrode cells. The analog-to-digital converter can convert the measured currents into a digital signal that is capable of being communicated to a computer.

In several embodiments, multiple footpads are used. In this configuration, the user terminal can record measurements of a patient striding from one footpad to the next.

Figure 4:
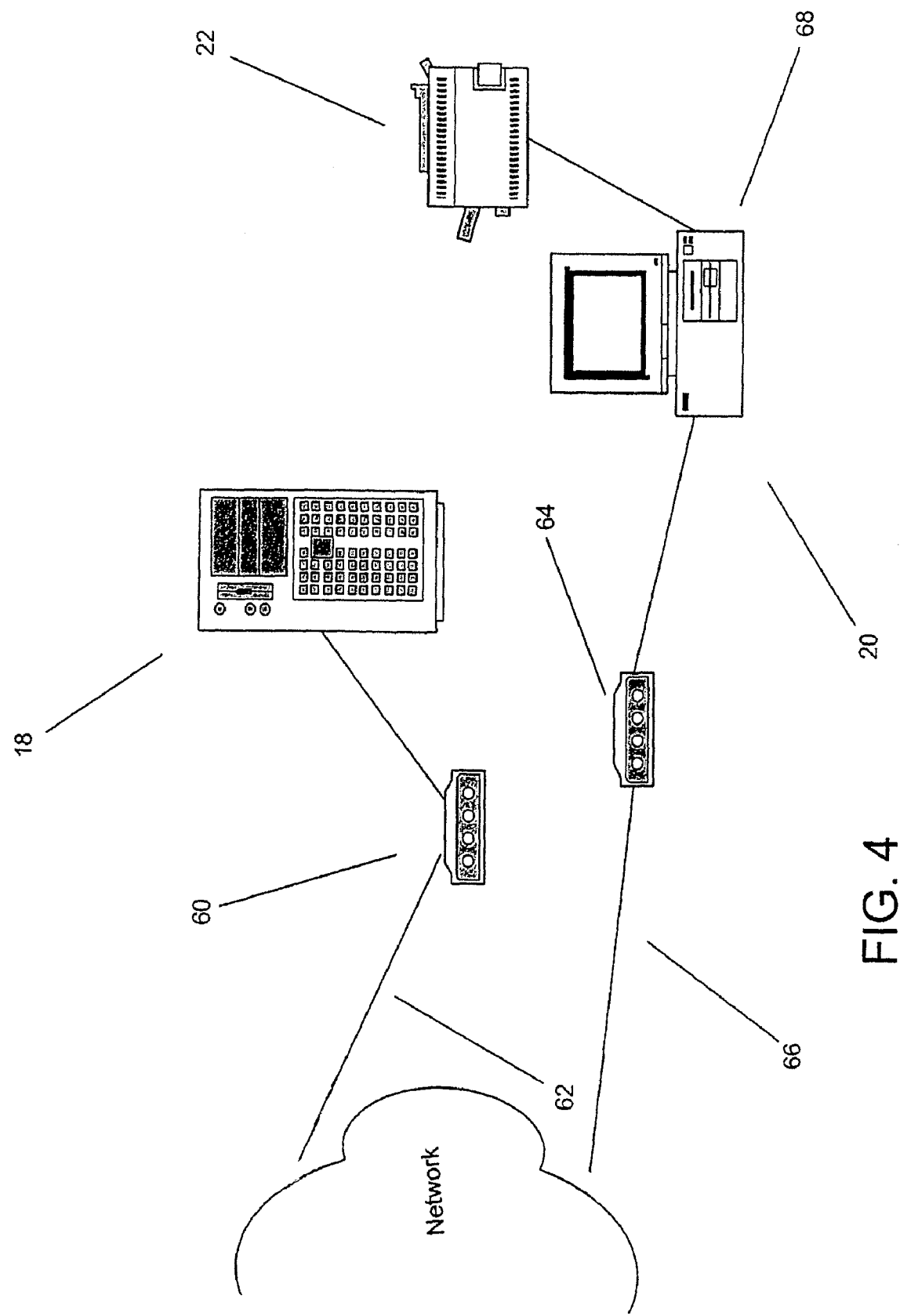
FIG. 4 is a schematic diagram of equipment located at a manufacturing facility in accordance with an embodiment of the present invention.

Equipment that can be located at a manufacturing facility in one embodiment of the present invention is illustrated in FIG. 4. The manufacturing facility can include a server 18 that is connected to a network. In one embodiment, the network is the telephone network and the server is connected to the network via a modem 60 connected to a telephone line 62. In other embodiments, the network is an Ethernet, the internet or another type of network over which digital information can be transferred and the server is connected to the network via an appropriate network interface. A manufacturing terminal 20 is also connected to the network via a modem 64 connected to a telephone line 66. The manufacturing terminal includes a computer 68 and a printer 22. Although the server is shown as being present at a manufacturing facility, in other embodiments the server can be located remote from the manufacturing facility.

The server receives three dimensional information concerning the shape of a patient's foot and performs analysis of this information to generate parameters that are useful in the manufacturing process. The information and the parameters are then transferred via the network to the manufacturing terminal, where a technician can view the information and be guided by the generated parameters in the selection of an orthotic shell that can then be modified to create an orthotic customized to the shape of the patient's foot. In one embodiment of the system, the technician has a number of different types of orthotic shells that can be used to create custom orthotics and the most appropriate shell is indicated by the parameters determined by the server from the three dimensional information of the patient's foot.

Figure 5:
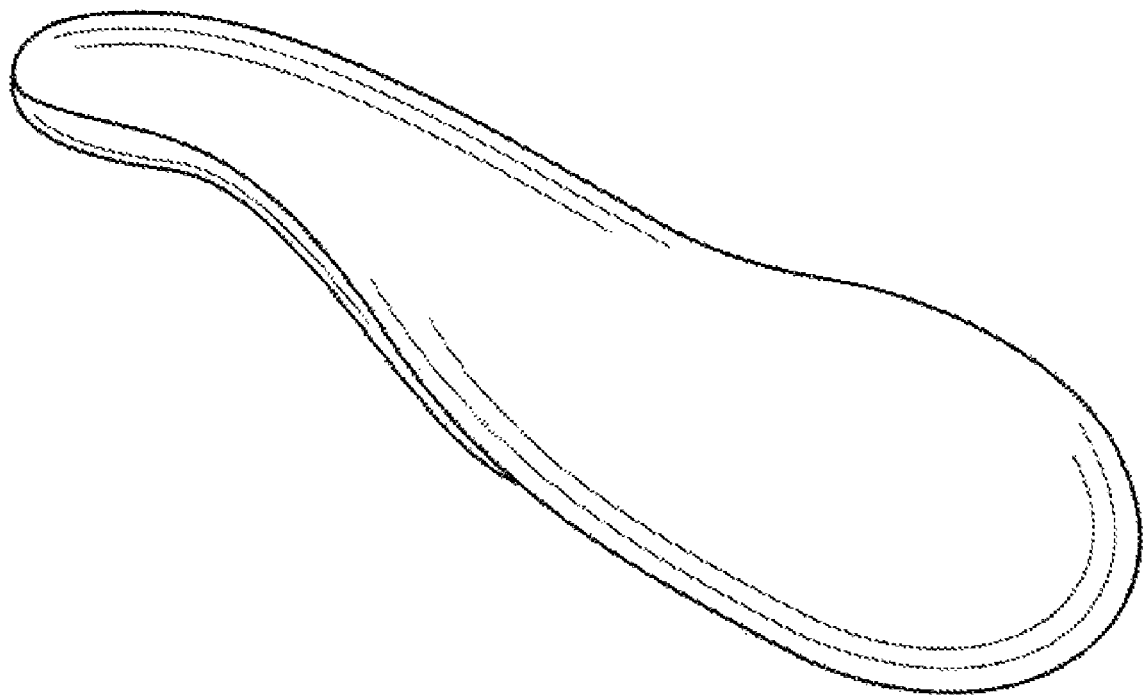
FIG. 5 is a perspective view of an orthotic shell capable of being used in conjunction with an embodiment of the method of the present invention.

An exemplary orthotic shell in accordance with an embodiment of the present invention is illustrated in FIG. 5. The shell can be modified using a heat gun or similar device to increase or decrease arch height or modify any other aspect of the orthotic shell's shape.

The hardware described above is operated in conjunction with software. The following provides a description of various software routines that can be used in accordance with embodiments of the present invention to operate the hardware described above.

Figure 6:
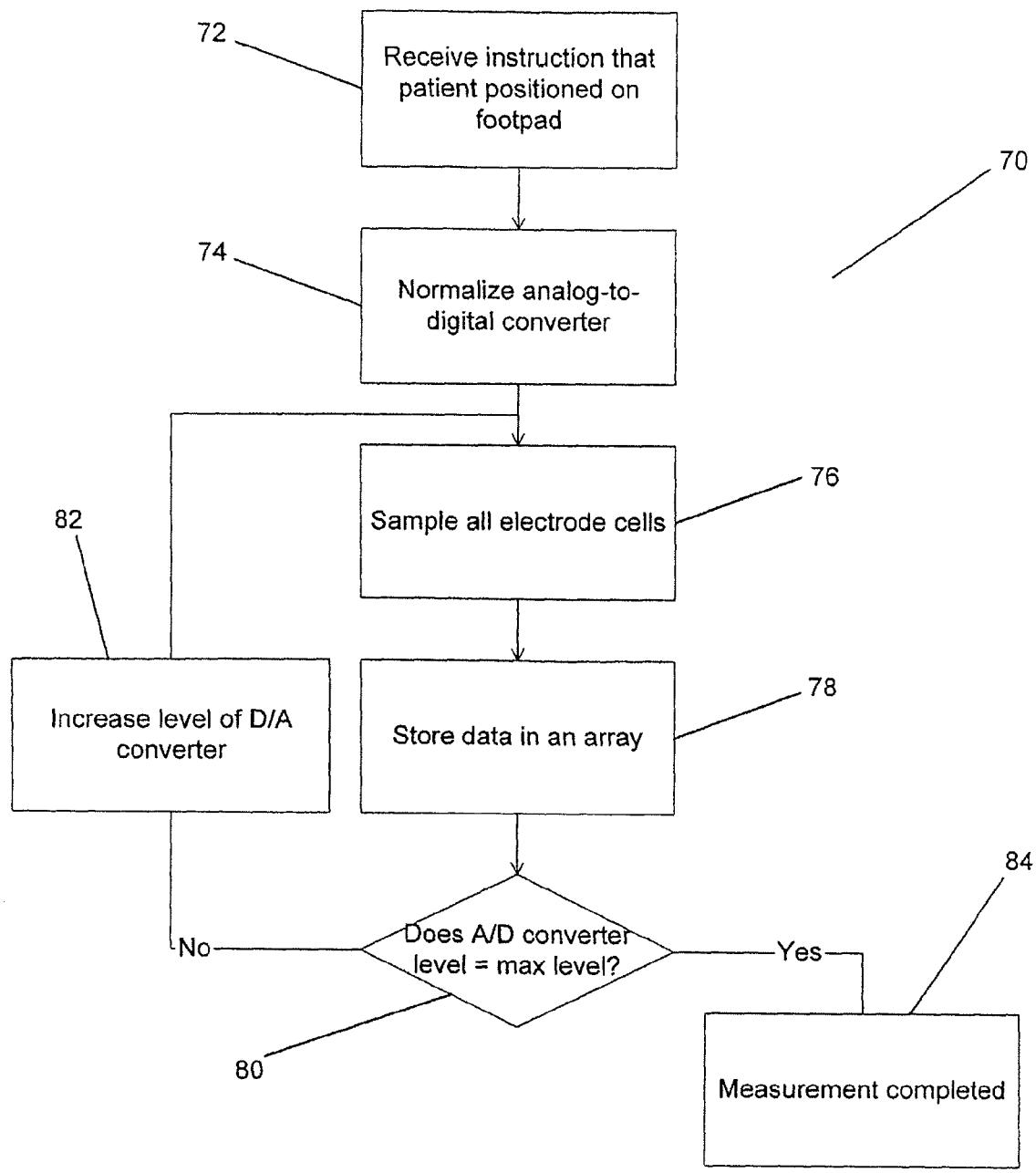
FIG. 6 is a flow diagram illustrating a method of capturing three dimensional information concerning the shape of a foot in accordance with an embodiment of the method of the present invention.

The user terminal 12 captures three dimensional information concerning the shape of a patient's foot. In one embodiment, software enables the hardware to capture this information statically and dynamically. A flow chart illustrating a process that can be implemented using the hardware described above and software for capturing three dimensional information of the shape of a patient's foot in accordance with an embodiment of the present invention is illustrated in FIG. 6. The process 70 includes detecting (72) that a patient is positioned on the footpad. The analog-to-digital converter is then normalized (74) using the bisection method to search the range of the analog-to-digital converter for the highest sensitivity level at which the analog-to-digital converter is not saturated. Once the analog-to-digital converter has been normalized, a sample of all the electrode cells is taken (76). The samples are stored (78) as an array in memory. The process is then repeated with increasing (82) levels for the analog-to-digital converter until the maximum level of the analog-to-digital converter is reached (80). In one embodiment, the range of sensitivities above the normalized level of the analog-to-digital converter is divided by six and six measurements are taken by adding the result of the division to the sensitivity of the previous measurement. Once the maximum level has been reached, the measurement is completed (84).

The normalization of the analog-to-digital converter enables the system to choose the level of sensitivity that provides the greatest amount of information for each patient. A heavier person will saturate many of the electrode cells at a high level of analog-to-digital converter sensitivity and a lighter person will generate currents that appear uniform at a low level of analog-to-digital converter sensitivity. By using the bisection method to locate the maximum sensitivity of the analog-to-digital converter, a data set can be obtained that possesses a significant range of values without saturation.

Figure 7:
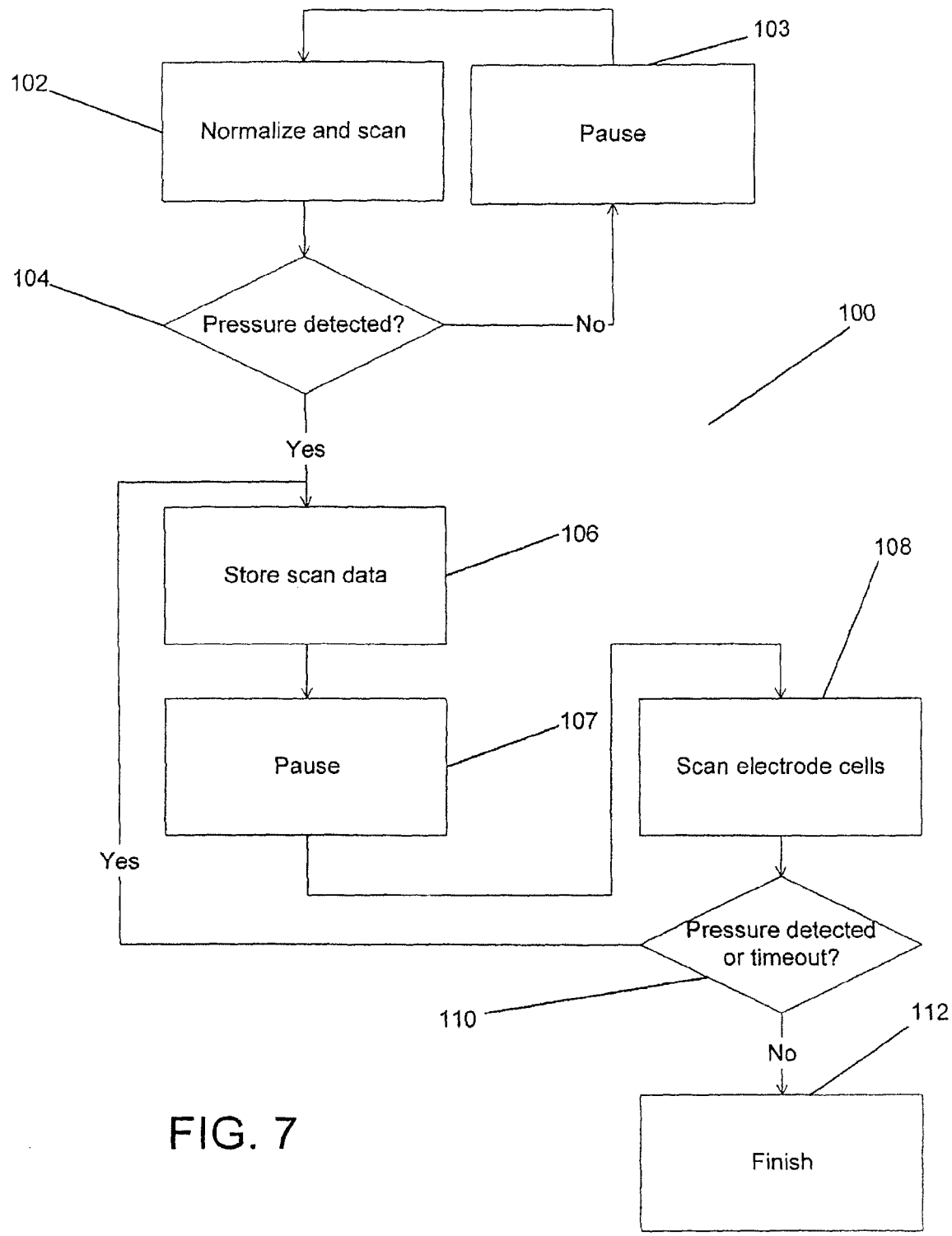
FIG. 7 is a flow diagram illustrating a method of dynamically capturing three dimensional information concerning the shape of a foot in motion in accordance with an embodiment of the method of the present invention.

A flow chart illustrating a process that enables the capture of three dimensional information concerning the shape of a patient's foot, when the foot is in motion, is shown in FIG. 7. The process 100 includes normalizing the analog-to-digital converter in the manner described above and then scanning (102) the electrode cells. If no pressure is detected, then the process pauses (103) and a new scan is taken until pressure is detected. Once pressure is detected (104), the scanned data is stored (106), a timer is started and the process pauses (107) before scanning (108) the electrode cells again. The scan is stored if pressure is detected (110). The process continues to scan and store data until pressure is no longer detected (110) on the footpad or the timer times out.

In addition to capturing information using the footpad, the user terminal in accordance with an embodiment of the present invention can display the captured information. The information can be displayed in one of a number of manners. In one embodiment, three dimensional information concerning the shape of a patient's foot can be displayed as a two dimensional height information display, a two dimensional interpolated height information display or a three dimensional contour map.

Figure 8:
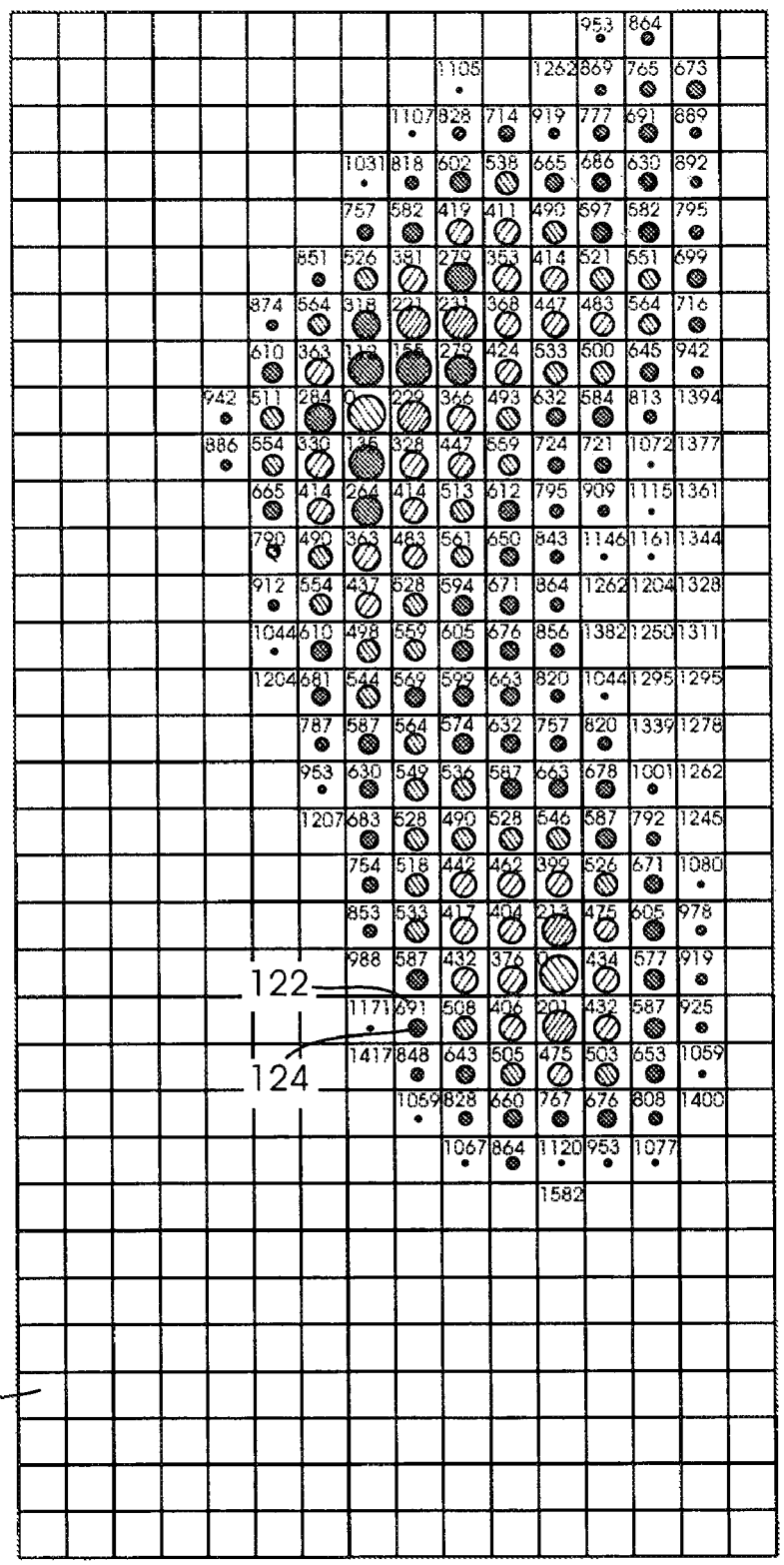
FIG. 8 is a schematic view of a graphical display of the topography of the bottom surface of a foot generated by a system in accordance with an embodiment of the present invention.

An example of a two dimensional height information display generated in accordance with an embodiment of the present invention is illustrated in FIG. 8. The display includes a grid 120 of cells. Each cell corresponds to information collected by an electrode cell in the footpad. The majority of cells do not contain information concerning the shape of a patient's foot and a 16×33 cell grid is chosen that contains all of the pressure information generated by the patient's foot.

The grid squares that contain pressure information concerning the patient's foot are indicated by a number 122 and a dot 124. The number indicates the height of the patient's foot at that point measured relative to the lowest point of the patient's foot. The size and color of the dot are assigned based on the height information. Numbers that are small are assigned large dots with a red color. As the number increases smaller dots with colors trending from red to yellow to green to blue are assigned. Cells where no pressure was detected from the patient's foot 126 are left empty.

Figure 9:
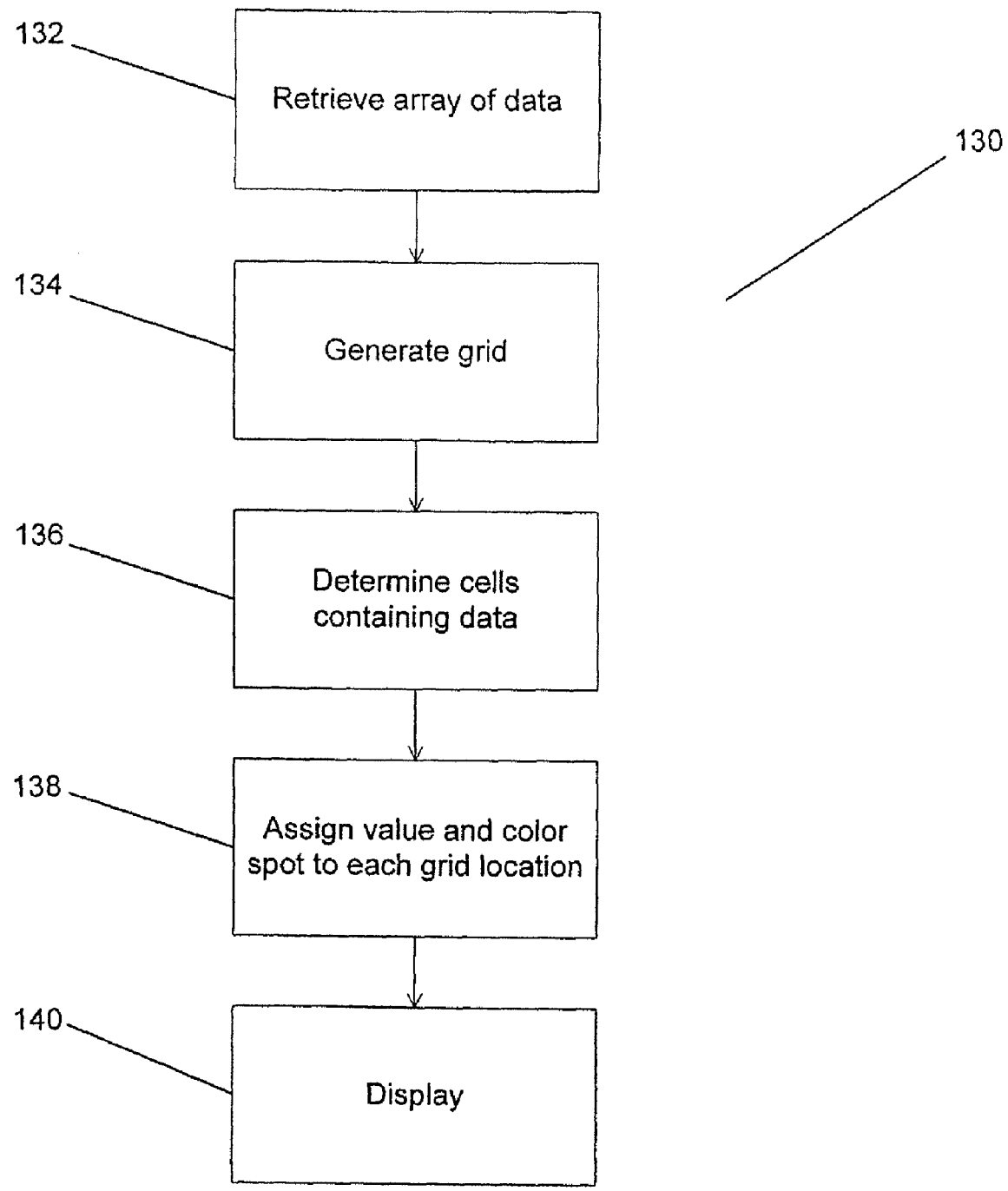
FIG. 9 is a flow diagram illustrating a process for generating a two dimensional height information display in accordance with an embodiment of the method of the present invention.

A process for generating a two dimensional height information display in accordance with an embodiment of the present invention is illustrated in FIG. 9. The process 130 includes retrieving (132) the appropriate array of data for display. A grid is generated (134) that is capable of being displayed on a computer screen. The portion of the stored array of data that contains information concerning the shape of the patient's foot is then determined (136) from the retrieved array of data. This data is then used to assign (138) numerical values and color spots to the grid locations corresponding to the electrode cells from which the data was recorded. The information is then displayed (140) on a computer screen. The information can also be converted to a format that is capable of being printed by a printer. In one embodiment, the software TeeChart distributed by Steema Software of Catalonia, Spain can be used to generate the display.

Figure 10:
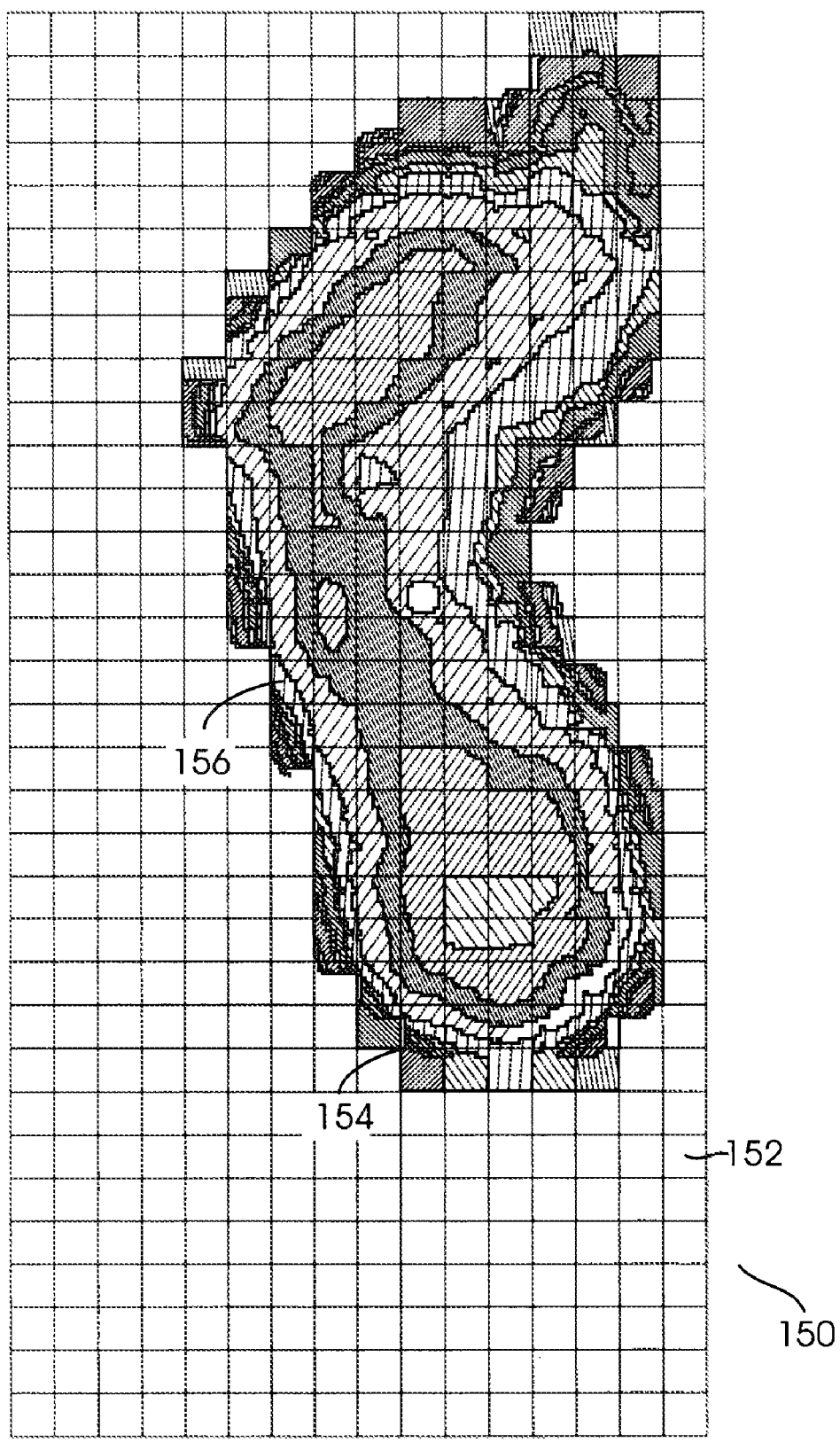
FIG. 10 is a schematic view of a two dimensional interpolated height graphic display generated in accordance with an embodiment of the present invention.

An example of a two dimensional interpolated height information display generated in accordance with an embodiment of the present invention is illustrated in FIG. 10. The image 150 includes a grid 152 that depicts the scale of the information presented. Superimposed on the grid are pixels of color that indicate the height of the surface of the underside of a patient's foot above an arbitrary reference surface. The information displayed has a higher resolution than the information collected using the footpad. The increased resolution is obtained by interpolating the raw data. A black dot 156 is superimposed on the image to indicate the center of balance of the foot.

Figure 11:
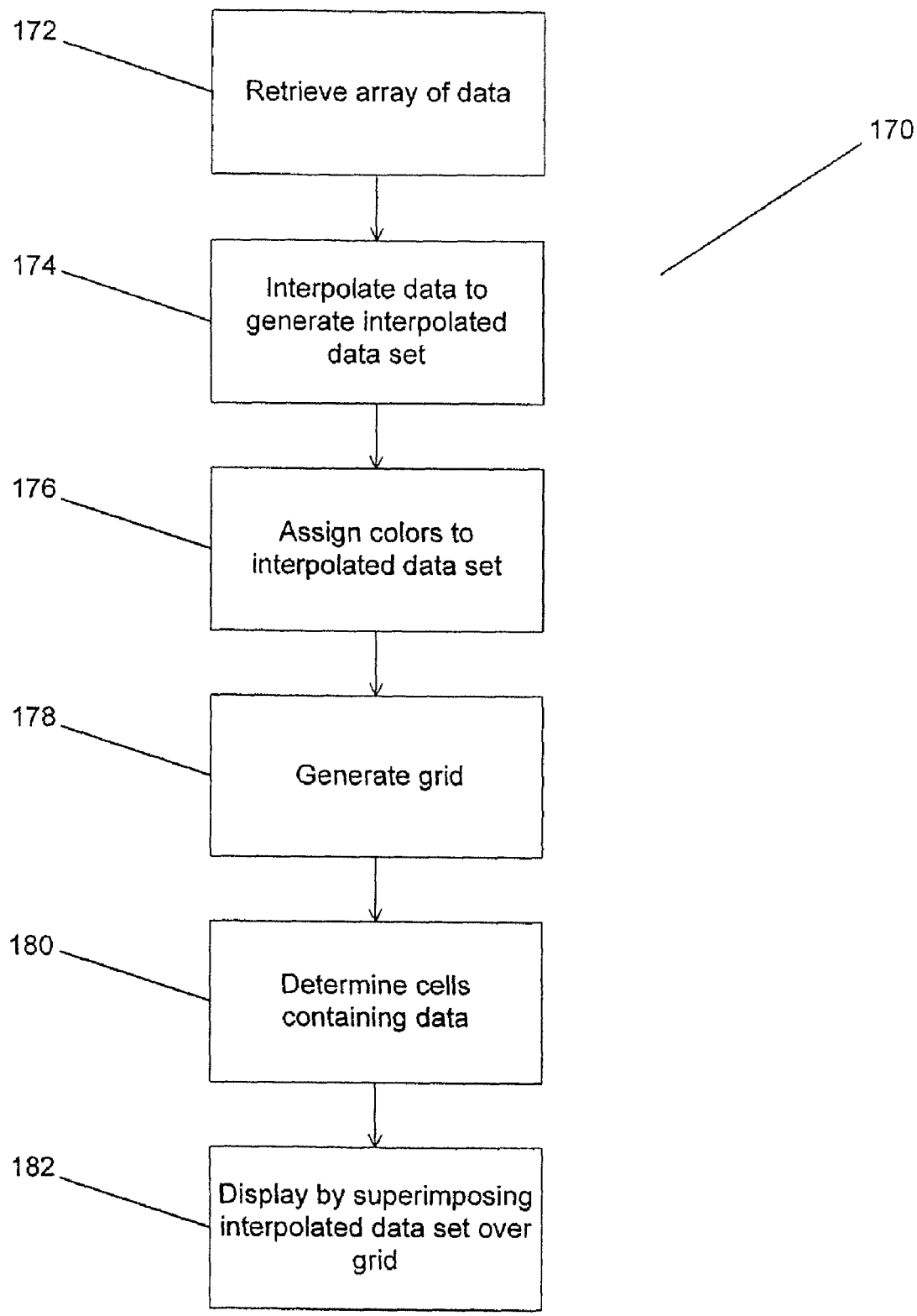
FIG. 11 is a flow diagram illustrating a process for generating a two dimensional interpolated height information display in accordance with an embodiment of the method of the present invention.

A process for generating a two dimensional interpolated height information display in accordance with an embodiment of the present invention is illustrated in FIG. 11. The process 170 includes retrieving (172) the relevant array of data. The data is then smoothed (174) to generate an interpolated data set. A commercial software routine such as Tee-Chart can be used to generate the interpolated data set. Once the interpolated data set is generated, each point of the interpolated data can be assigned (176) a color based on the relative height of point above the base of the footpad. A grid is then generated (178) and the cells of the grid that include interpolated data are identified (180). The data can then be displayed (182) by superimposing the data over the relevant squares of the grid.

Figure 12:
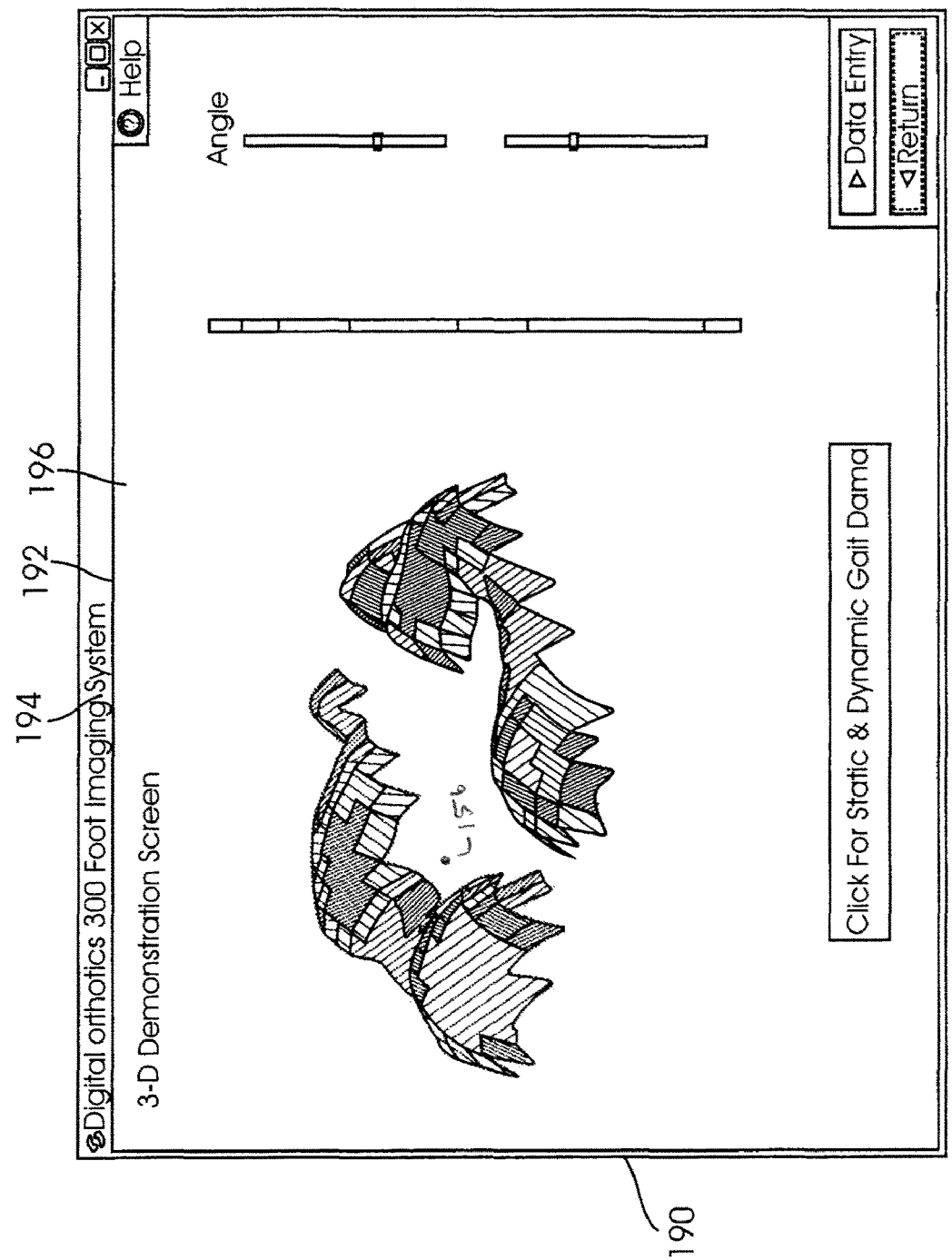
FIG. 12 is schematic view of a three dimensional contour map generated in accordance with an embodiment of the present invention.

An example of a three dimensional contour map generated in accordance with an embodiment of the present invention is illustrated in FIG. 12. The image 190 includes a three dimensional contour map 192 of each foot. The contour map uses a combination of contour lines 194 and color 196 to create the illusion of a three dimensional surface on the two dimensional computer screen. The contour lines and the colors are chosen to represent a three dimensional shape corresponding to the surface of the patient's foot.

Figure 13:
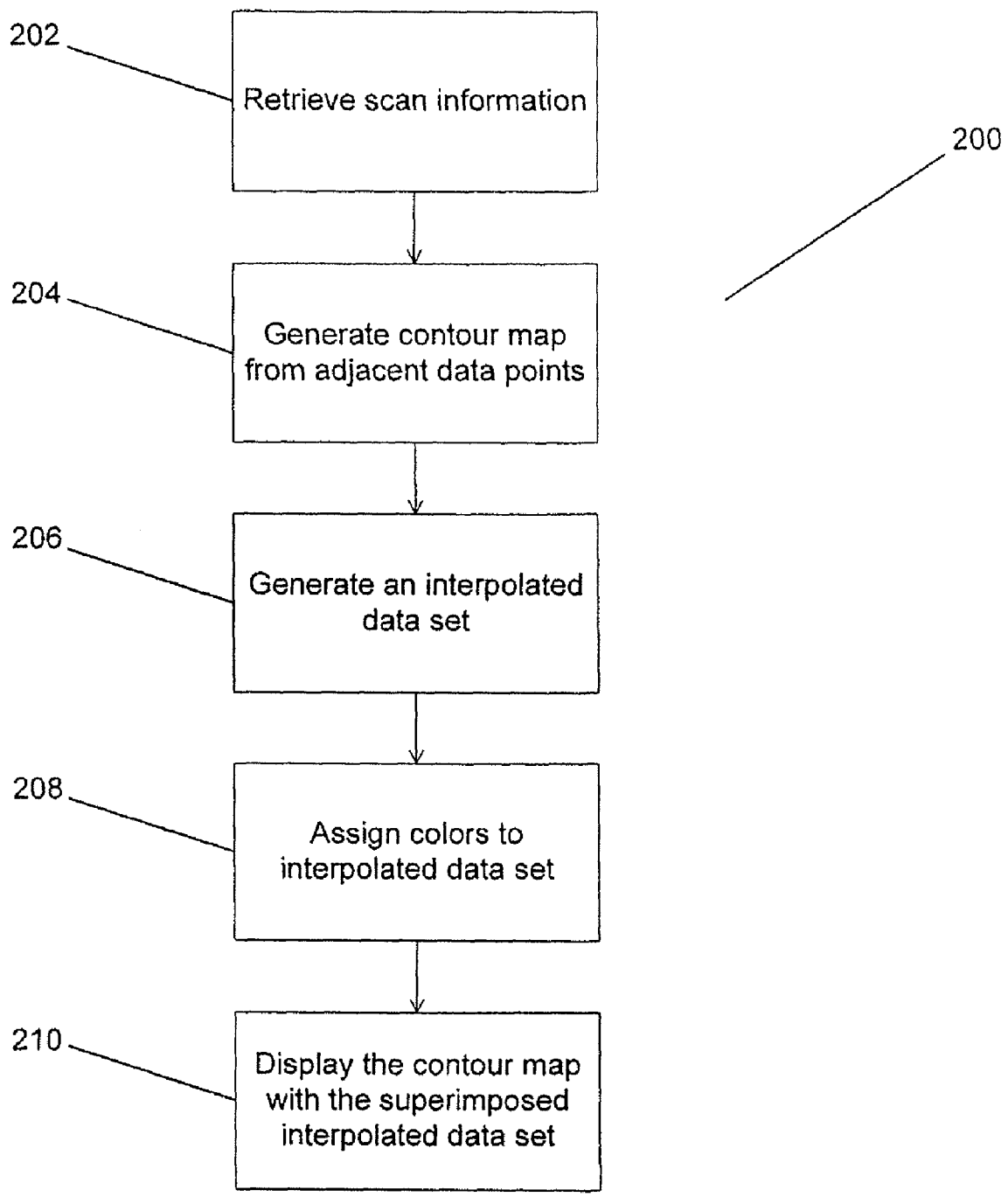
FIG. 13 is a flow diagram illustrating a process for generating a three dimensional contour map in accordance with an embodiment of the present invention.

A process for generating a three dimensional contour map in accordance with an embodiment of the present invention is illustrated in FIG. 13. The process 200 in accordance with the present invention includes retrieving (202) the scan information and generating (204) a contour map using adjacent data points. In one embodiment, a commercial contour mapping engine such as TeeChart can be used to generate the contour map. The retrieved information can also be used to generate (206) an interpolated data set in the manner described above in relation to FIG. 11. Once colors are assigned to the interpolated data set to represent the relative height of each of the data points, the interpolated data set is superimposed (210) onto the contour map. The contour map and the superimposed interpolated data set are then displayed (212).

Figure 14:
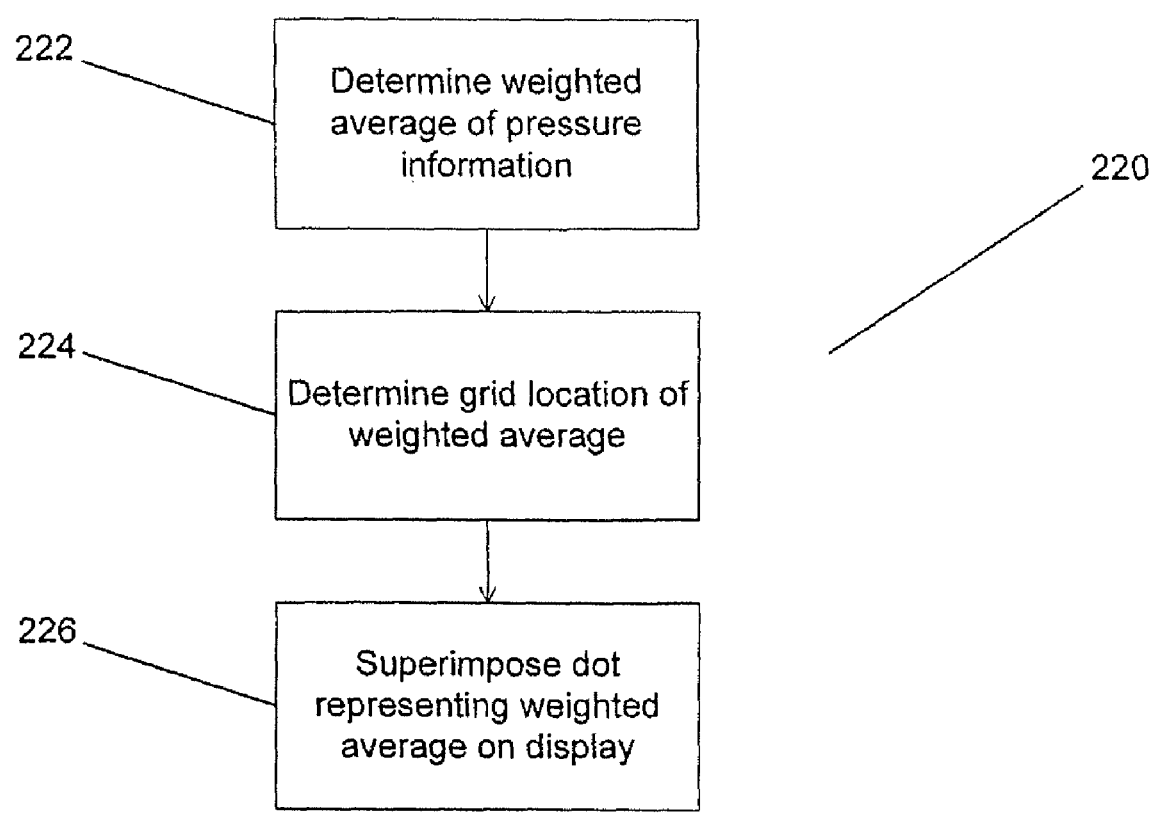
FIG. 14 is a flow diagram illustrating a process for calculating the location of the center of mass of the force exerted on a footpad by the patient's foot.

Referring back to FIG. 12, the center of balance 156 is shown as black dot superimposed on the image of the patient's foot. A process that can be used in accordance with one embodiment of the present invention to calculate the location of the center of mass of the force exerted on the footpad by the patient's foot is illustrated in FIG. 14. The process 220 involves taking (222) a weighted average of the grid co-ordinates of the data points. Each grid location is weighted according to the amount of pressure exerted on that grid cell by the patient's foot. The amount of pressure is determined using the height data collected using the footpad. The weighted average is the center of balance. The grid location of the center of balance is determined (224) and then superimposed (226) over the height information display. The center of balance can be superimposed over whichever display mode is being used to display the height information collected by the footpad.

As discussed above, a user terminal in accordance with an embodiment of the present invention is capable of capturing information dynamically. Dynamic information capture can be used to obtain information concerning the manner in which the undersurface of a patient's foot changes shape as the patient walks or runs.

Figure 15:
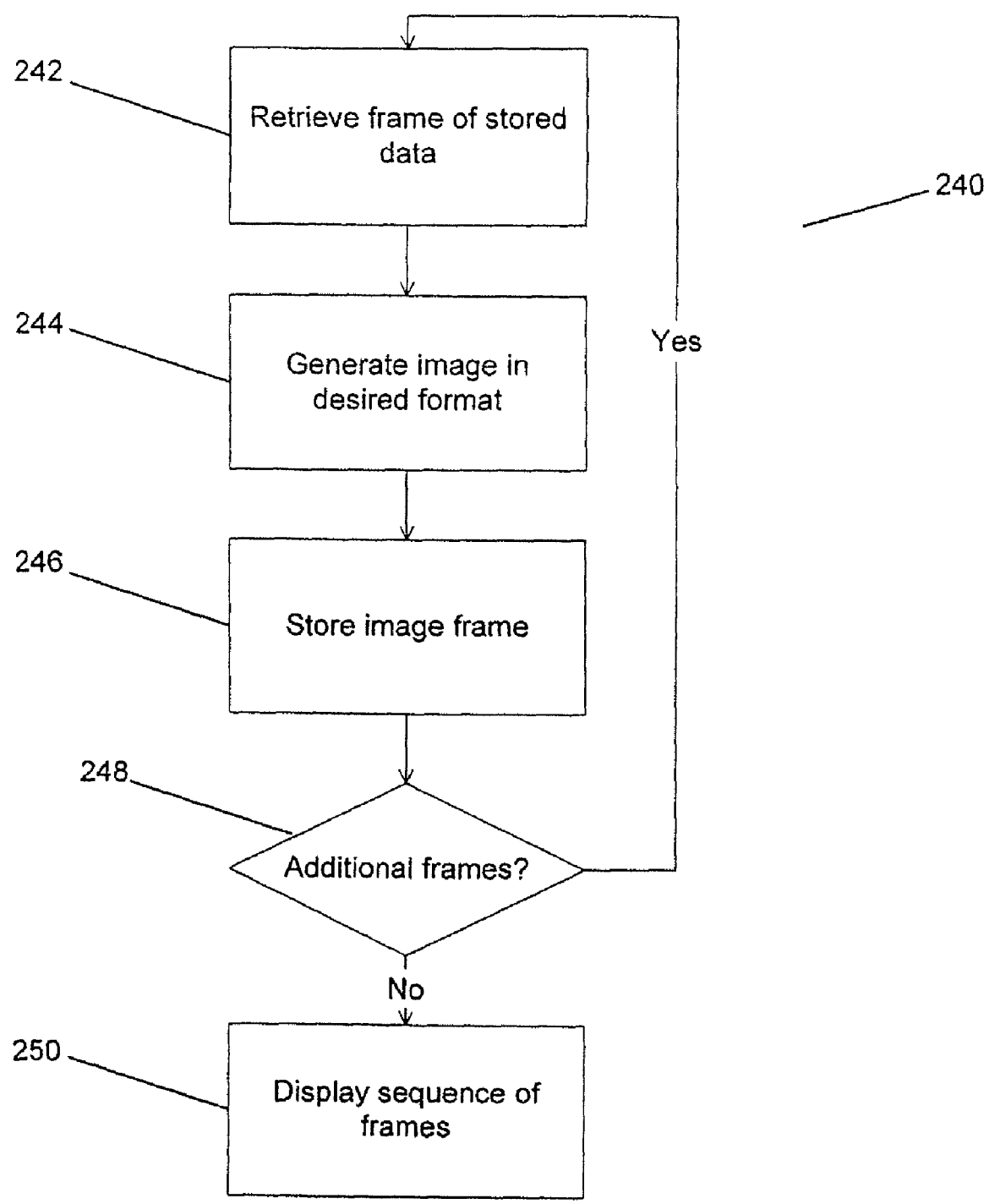
FIG. 15 is a flow diagram illustrating a process for displaying information concerning the shape of a foot during dynamic contact with a sensing surface in accordance with an embodiment of the method of the present invention.

An embodiment of a process for obtaining information concerning the shape of a patient's foot during motion was described above in relation to FIG. 7. A process in accordance with an embodiment of the present invention for displaying information concerning the shape of a patient's foot during motion is illustrated in FIG. 15. The process 240 includes retrieving (242) a first frame of stored data. The frame of data is then processed to generate an image in a desired format. Typically the desired format will be either a two dimensional interpolated height information display or a three dimensional contour map. The two dimensional interpolated height information display or the three dimensional contour map can be generated in accordance with the description provided above. The image frame is then stored (246) and a determination (248) is made as to whether any additional frames of data were captured. If additional frames of data exist, then each of these frames is retrieved and an image in the desired format is generated and stored. The process repeats until no additional frames of data remain. Once images have been generated from each of the frames of data, then the sequence of image frames can be displayed (250) on a computer screen. If sufficient processing power exists, the display of the image frames can occur simultaneously with the generation of the images for later frames of data.

In addition to displaying information concerning the shape of a patient's foot, user terminals in accordance with the present invention are capable of analyzing a patient's gait. During the display of the dynamic information, the user terminal can show the location of the center of balance in each frame, display the elapsed time, the percentage and duration of time spent on three important phases of the gait cycle (i.e. the contact, midstance and propulsive phases) and/or the "gait line", which is a composite of all of the center of balance for each frame of the dynamic information.

Figure 16:
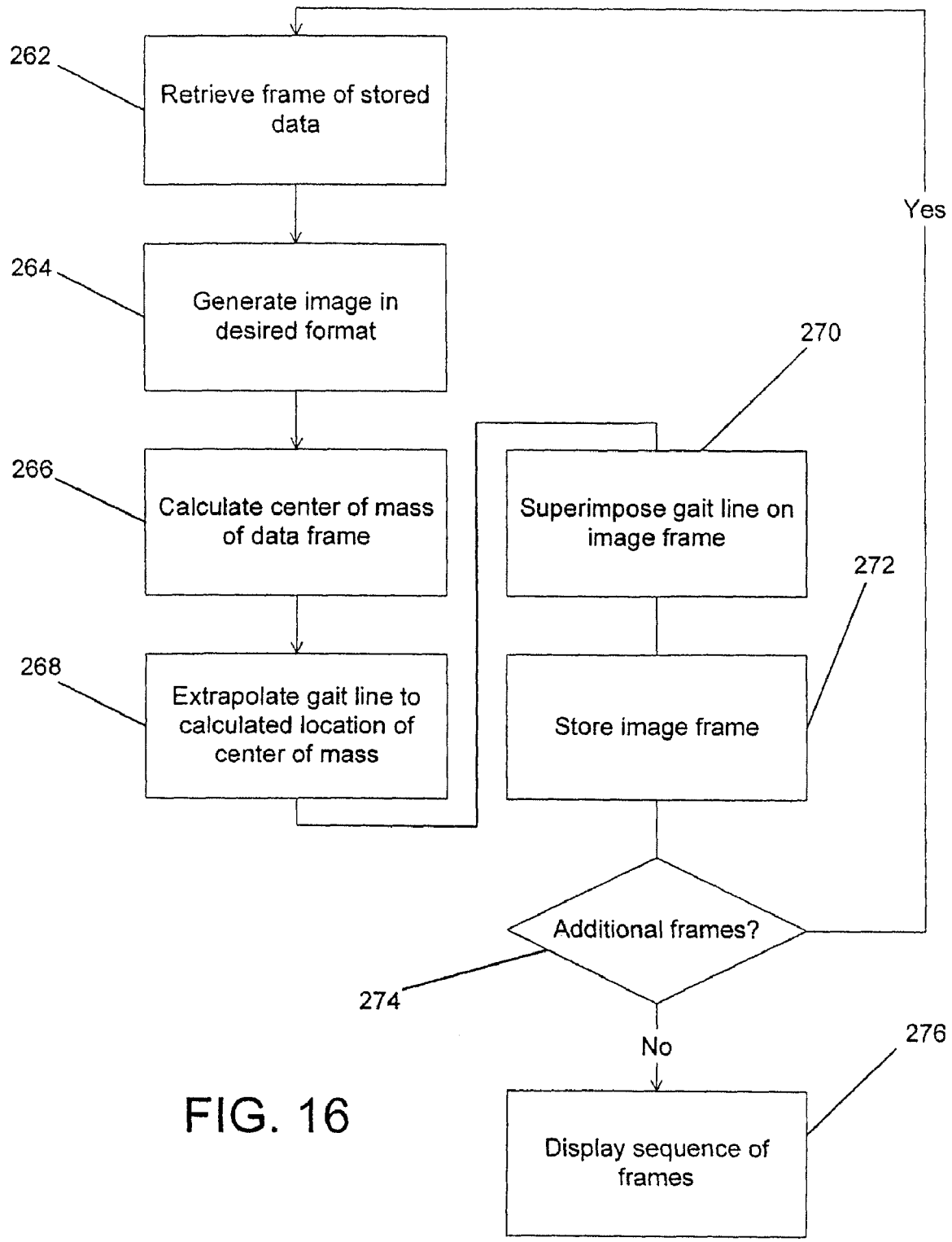
FIG. 16 is a flow diagram illustrating a process for generating a "gait line" in accordance with an embodiment of the method of the present invention.

In one embodiment, the center of balance in each frame is calculated using the process described above in relation to FIG. 14. The "gait line" is simply a line corresponding to the change in the location of the center of balance as the patient's foot contacts the footpad and then lifts from the footpad. An embodiment of a process in accordance with the present invention for generating a "gait line" from frame data captured using a footpad is illustrated in FIG. 16. The process 260 includes retrieving (262) a first frame of data. The retrieved data is used to generate (264) an image frame in a desired format in a similar manner to that discussed above in relation to FIG. 15. The center of balance for the frame is then calculated using the retrieved data in a manner similar to that described above in relation to FIG. 14. The location of the center of balance is then used to form the "gait line". The "gait line" starts at the location of the center of balance for the initial frame and then is formed (268) by extrapolating from the center of mass from the previous frame to the center of mass of the current frame. The "gait line" is then superimposed (270) on the image frame and the result is stored (272). If there are additional frames of data (274), then the process is repeated. Otherwise the sequence of image frames can be sequentially displayed (276) on a computer screen.

In other embodiments, a similar process can be used simply to generate the "gait line" without generating the image frame information. The "gait line" can then be superimposed on a static image of the patient's foot.

Figure 17:
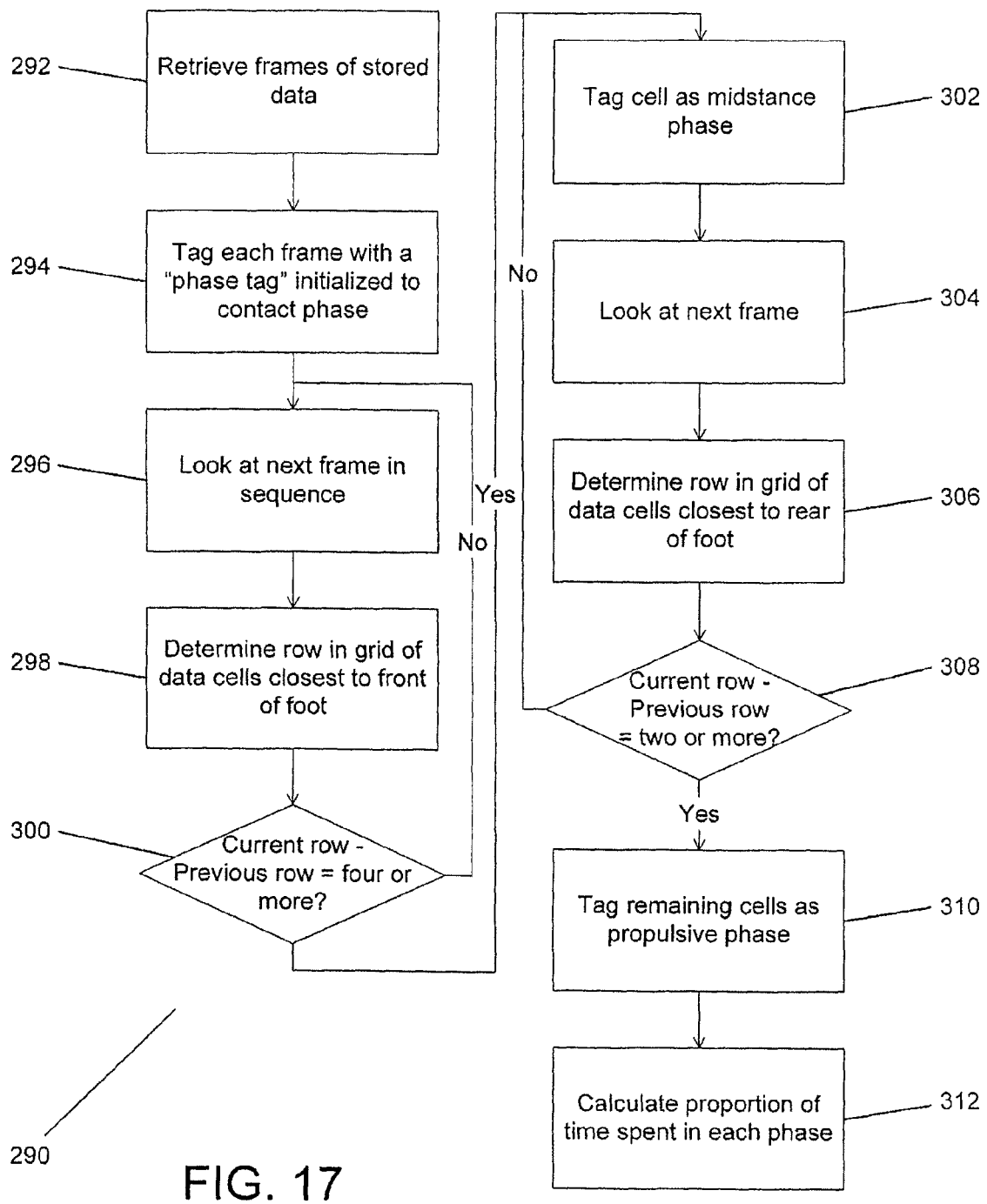
FIG. 17 is a flow diagram illustrating a process for calculating the percentage of time spent in each of the contact, midstance and propulsive phases of a gait cycle in accordance with an embodiment of the method of the present invention.

An embodiment of a process in accordance with the present invention for calculating the percentage of time spent in each of the contact, midstance and propulsive phases of the gait cycle is illustrated in FIG. 17. The process 290 involves retrieving (292) frames of stored data and tagging (294) each frame with a "phase tag" that is initialized to indicate the contact phase of the patient's gait. Once each "phase tag" has been initialized, the first frame is examined (296) to determine (298) the row number of the row of cells that contain data and are closest to the front (i.e. the end of the toes) of the patient's foot. Then the next frame in the sequence of frames is examined (296) to determine the row number of the row of cells that contain data and are closest to the front of the foot. The two row numbers are compared (300) and if they differ by four or more, then the second frame in the sequence of frames is tagged (302) as being part of the midstance phase in the gait cycle. If the row numbers of the frames do not differ by four or more, then the next frame in the sequence of frames is examined (296) and the frame is compared (300) with the previous frame until there are no more frames or the difference in the row numbers is four or more. Once a midstance frame has been identified, the process of examining frames (304, 306, 308) and comparing them to previous frames continues. However, the comparison (308) is made with a view to determining whether the row number of the row that is closest to the back of the foot (i.e. the heel) is two or more greater than the equivalent row number for the previous frame. Once a frame is located where the row number of the row of cells that contain data and are closest to the back of the foot is two or more greater than the previous frame, then that frame and all subsequent frames are tagged (310) as being part of the propulsive phase of the gait cycle. The proportion of the gait cycle spent in each phase can then be calculated (312) by determining the number of frames tagged as being part of each phase as a proportion of the number of frames in the gait cycle.

Figure 18:
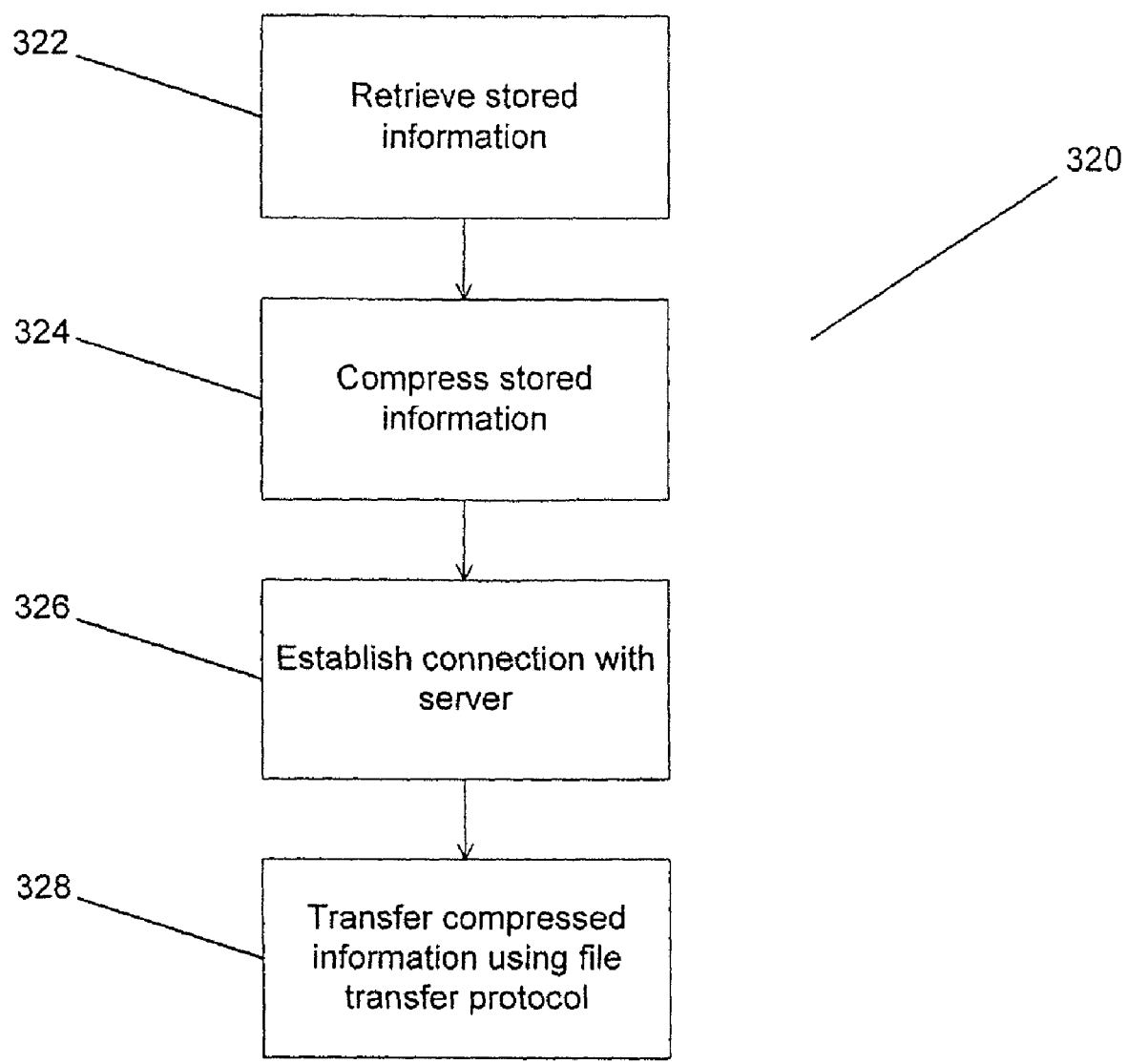
FIG. 18 is a flow diagram illustrating a process for storing patient information and transferring the information to a server in accordance with an embodiment of the method of the present invention.

As described above, the user terminal can store the raw information obtained from the footpad in a database and then transmit the information to a server. An embodiment of a process in accordance with the present invention for storing the information and then transferring the information to a server is illustrated in FIG. 18. The process 320 includes retrieving (322) the stored information that is to be sent to the server. The retrieved information is compressed (324) a connection is established with a server and the compressed information is transferred (326) to the server using a file transfer protocol.

In other embodiments, other techniques involving the transfer of digital information can be used to transfer the three dimensional information concerning the shape of a patient's foot to a server. In other embodiments, additional information such as the image information that can be displayed using a computer is also transferred.

As discussed above, a server receives information transmitted by user terminals, stores the information in a database, performs operations to obtain custom fitting parameters and transfers the information and the custom fitting parameters to a manufacturing terminal.

Figure 19:
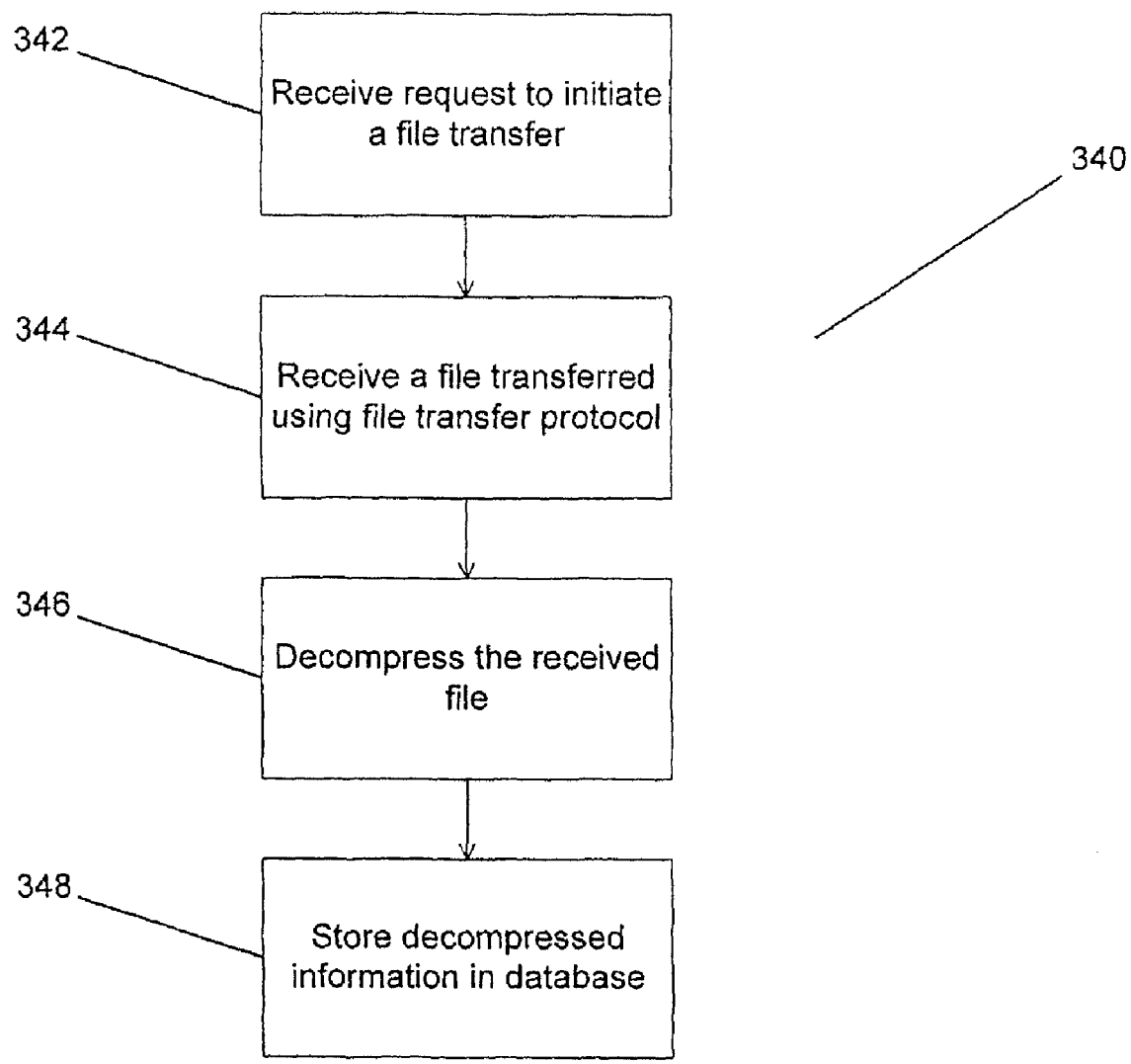
FIG. 19 is a flow diagram illustrating a process in accordance with the present invention for receiving and storing patient information transmitted by a user terminal over a network in accordance with an embodiment of the method of the present invention.

An embodiment of a process in accordance with the present invention for receiving and storing information transmitted by a user terminal over a network is illustrated in FIG. 19. The process 340 includes receiving (342) a request to initiate a file transfer. Receiving (344) a file transferred using the file transfer protocol. Decompressing (346) the file to yield three dimensional information concerning a patient's foot and then storing (348) the information in a database.

Similar methods to those illustrated in FIGS. 18 and 19 can be used to transfer data between a server and a manufacturing terminal.

A server in accordance with an embodiment of the present invention can analyze the three dimensional information concerning the shape of a patient's foot that is provided by a user terminal. In one embodiment, the server analyzes the three dimensional information to obtain custom fitting parameters such as the arch height of the patient's foot, center of balance for each foot and center of balance for the patient. In several embodiments, batch processing of three dimensional information is performed. In other embodiments, three dimensional information is analyzed as it is received.

Figure 20:
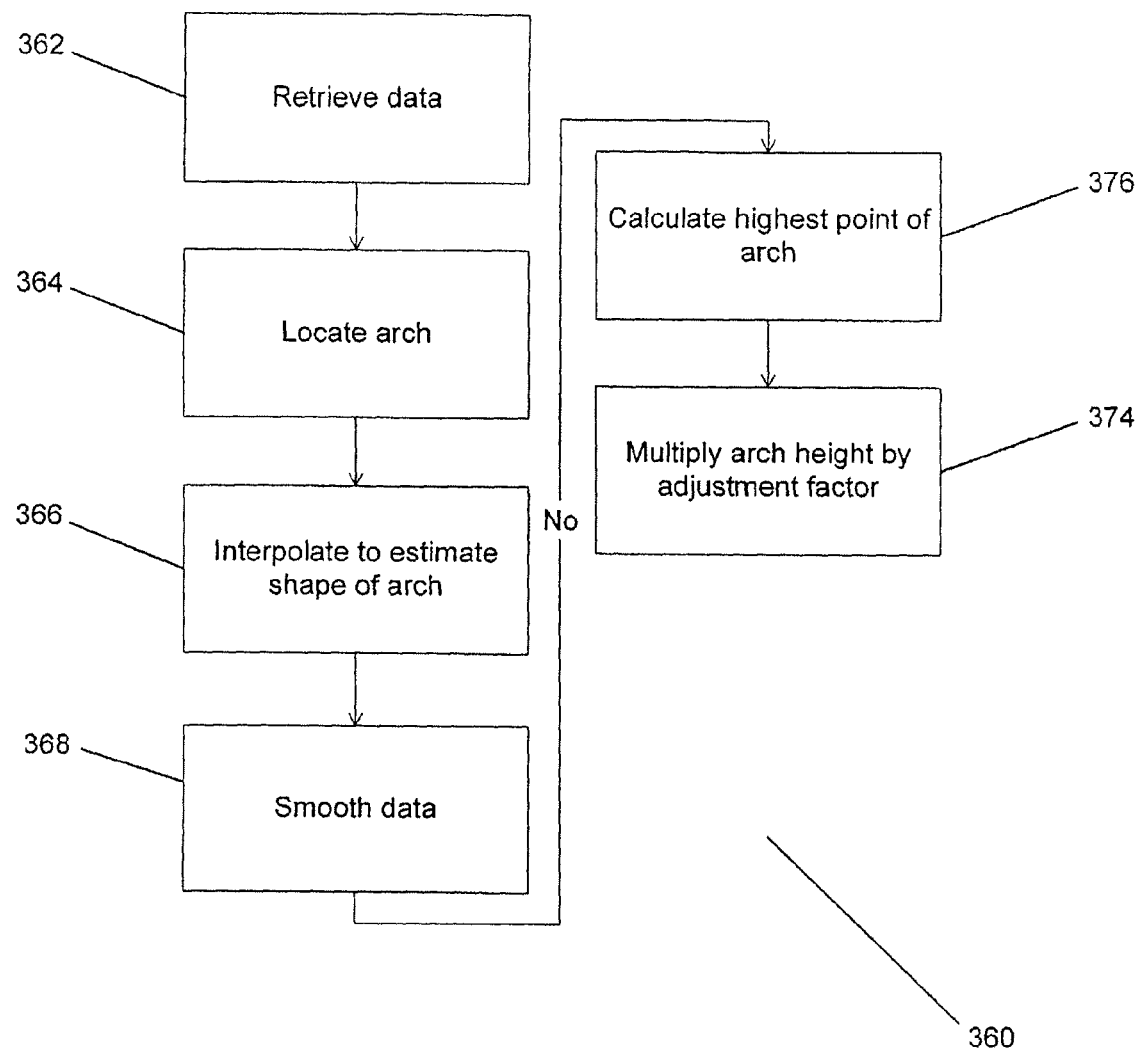
FIG. 20 is a flow diagram of a process for obtaining the arch height of a patient's foot from three dimensional information provided by a user terminal in accordance with an embodiment of the method of the present invention.

An embodiment of a process in accordance with the present invention for obtaining the arch height of a patient's foot from the three dimensional information provided by a user terminal is illustrated in FIG. 20. The process 360 involves retrieving (362) the three dimensional information concerning the shape of the patient's foot. The arch of the patient's foot is then located (364). The arch can be located by ignoring the first column of data on the arch side of the foot and then locating a trapezoid of 15 cells (a column of 9 cells adjacent a column of 7 cells adjacent a column of 5 cells) that has the highest average height. The arch height can then be determined by interpolating (366) the cells. The interpolation can be determined by curve fitting the information possessed in relation to each of the fifteen cells. The interpolated data is then smoothed (368). The arch height is then determined (376) as the highest point of the smoothed interpolated arch data. Depending on whether a patient has a hypermobile, rectus or cavus foot, the value of the arch height is multiplied (374) by an adjustment factor. The adjustment factor serves to correct problems associated with the manner in which the patient's foot moves during his or her gait. In one embodiment, the calculated arch height value of a hypermobile foot is adjusted by a factor of 2.5. The arch height of a rectus foot is adjusted by a factor of 1.5 and the arch height of a cavus foot is adjusted by 0.5. In other embodiments, other adjustment factors for correcting gait abnormalities can be used.

In several embodiments, position arrows are displayed on the images of a patient's foot displayed on a manufacturing or user terminal. These position arrows show the center of balance for each of a patient's feet and the patient's overall center of balance. The location of the position arrows can be determined by taking a weighted average in the manner described above. The position arrows can be supplemented with information showing a "normal" range of values for the location of the various centers of balance.

Figure 21:
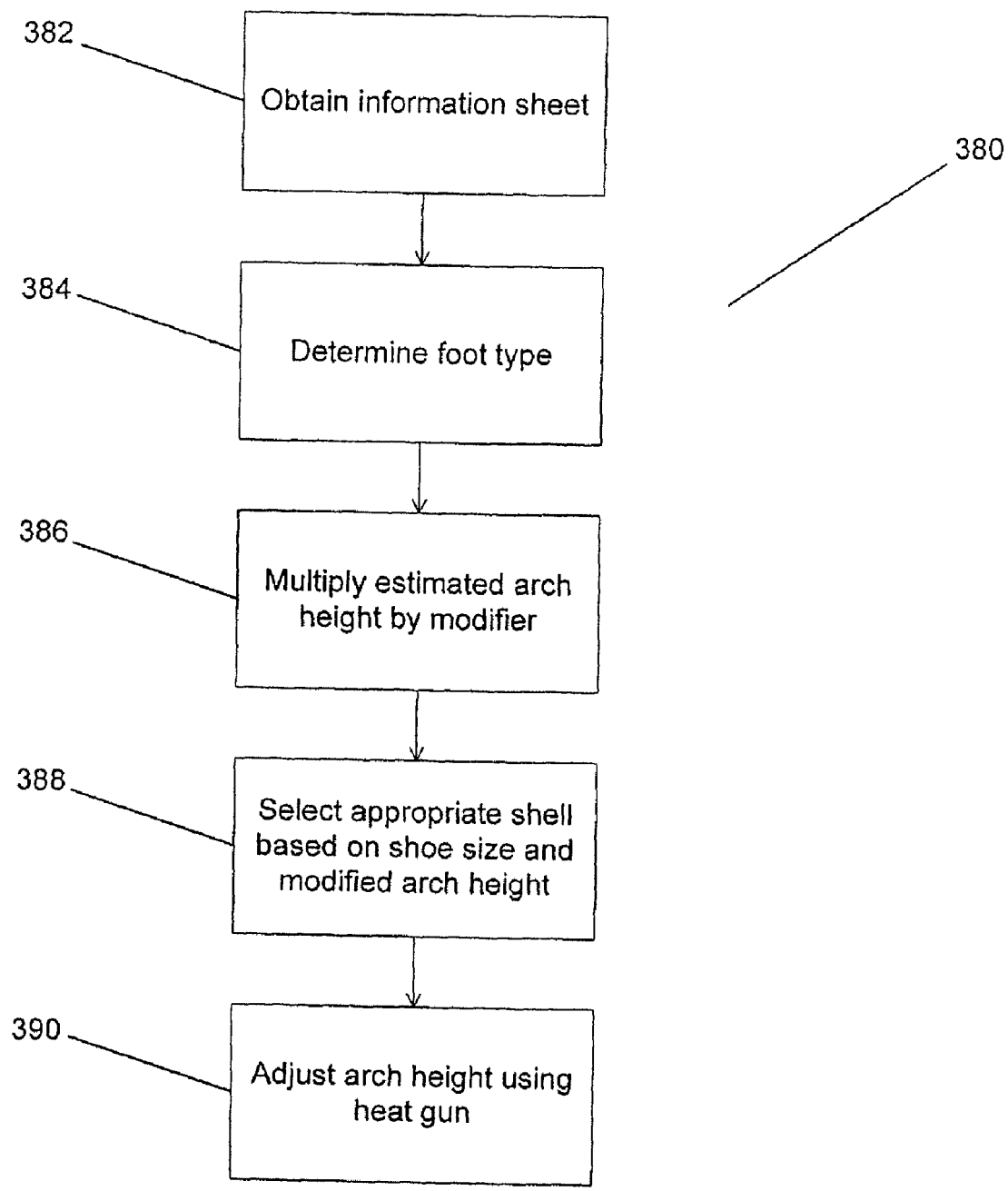
FIG. 21 is a flow diagram of a process for selecting an orthotic shell in accordance with an embodiment of the method of the present invention.

As discussed above, the server provides the three dimensional information concerning the shape of a patient's foot and the custom fitting parameters to a manufacturing terminal via the network. This information is used for the manufacturing of an orthotic customized to fit the patient's foot. A process that can be used by a technician in accordance with the practice of the present invention to select an orthotic shell from which to make the custom fitted orthotic is illustrated in FIG. 21. The process 380 includes obtaining (382) an information sheet that includes the estimated arch height of each of the patient's feet (determined as described above). The technician then determines the patient's foot type (384) by examining the two dimensional height information displays and video of the patient's gait and modifies (386) the arch height in the manner described above in accordance with the foot type. In other embodiments, the patient's foot type can be specified by the doctor and modification performed automatically and provided to the technician. The foot size and modified arch height are then used to select (388) an orthotic shell, similar to the shell illustrated in FIG. 5, having a shape closest to the required shape. The arch height of the orthotic shell can then be adjusted (390) using a heat gun to achieve the desired shape. In other embodiments, software can be used to control one or more machine tools to automate the process of manufacturing an orthotic.

Although the foregoing embodiments are disclosed as typical, it would be understood that additional variations, substitutions and modifications can be made to the system, as disclosed, without departing from the scope of the invention. For example, other distributions of the functions of the system across the various elements of the system could be used to obtain information, process information and manufacture orthotics using the processed information. Accordingly, the scope of the invention should be determined not by the embodiments illustrated, but by the appended claims and their equivalents.

What is claimed is:

1. A system for manufacturing custom orthotics comprising:
    a sensor pad for acquiring three dimensional information concerning a topography of a sole of a patient's foot, the sensor pad for acquiring utilizing pressure applied by the patient's foot and comprises a plurality of electrode cells comprising piezoelectric materials for acquiring static, dynamic, or both static and dynamic topography information;
    means for communicating the topography information:
    a server for receiving the topography information and analyzing the topography information;
    a display for displaying the topography information and the analysis of the topography information;
    wherein the three dimensional information includes an array of data describing the topography of portions of the patient's foot; and
    the displayed topography information comprises information from at least seven cells each having a highest average height value.

2. The method of claim 1, further comprising selecting an orthotic shell from a plurality of different types of orthotic shells and modifying the selected shell based on the analysis to more clearly match the analyzed topography information to manufacture a custom orthotic.

3. The method of claim 1, wherein the analysis obtains information concerning the patient's center of balance, which comprises, at least in part, a weighted average of a grid coordinate of data points weighted according pressure exerted on respective electrode cells by the patient's foot.

4. A method of manufacturing a custom orthotic, comprising:
    acquiring measurements in three dimensions concerning a shape of a patient's foot, the acquiring measurements utilizing pressure of the patient's foot on a sensor pad;
    analyzing the measurements;
    displaying the measurements and the analysis,
    the measurements include an array of data describing the topography of portions of the patient's foot gathered from a plurality of electrode cells comprising piezoelectric materials located in the sensor pad; and the analysis obtains information concerning the patient's arch, which comprises locating a trapezoid of cells that has highest average heights of reviewed cells and selecting points among the reviewed cells.

5. The method of claim 4, wherein three dimensional info a on includes information acquired while the patient is stationary and information acquired while the patient is in motion.

6. The method of claim 4, wherein the analysis obtains information concerning the patient's center of balance, which comprises, at least in part, a weighted average of a grid coordinate of data points weighted according pressure exerted on respective electrode cells by the patient's foot.

7. The method of claim 4, wherein the analysis obtains information concerning the patient's gait line.

8. The method of claim 4, wherein the analysis obtains the proportion of time spent in the contact, midstance and propulsive phases of a gait cycle.

9. The method of claim 4, wherein the display is in the form of a printed information sheet.

10. The method of claim 4, wherein the acquiring is performed while the patient's foot is statically contacting the sensor pad.

11. The method of claim 4, further comprising selecting an orthotic shell from a plurality of different types of orthotic shells based on the analysis.

12. The method of claim 4, further comprising selecting an orthotic shell from a plurality of different types of orthotic shells and modifying the selected shell based on the analysis to form a custom orthotic.

13. The method of claim 12, wherein a heat gun is utilized in modifying the selected shell.

14. The method of claim 12, where modifying the selected shell includes changing arch height.

15. A system for manufacturing custom orthotics comprising:
    a reader for acquiring three dimensional information concerning a topography of a sole of a patient's foot when the foot is in contact with the reader, the reader utilizes pressure applied by the patient's foot to acquire the topography information;
    a transmitting device for communicating the topography information;
    a server for receiving the topography information and for analyzing the topography information;
    a display for displaying the topography information and the analysis of the topography information; and
    wherein the three dimensional information includes an array of data describing the topography of portions of the patient's foot and the display of topography information comprises a display of two dimensional interpolated height information with a center of balance display of the patient's foot superimposed on the two dimensional interpolated height information.

16. The system of claim 15, further comprising a plurality of different types of orthotic shells having different shapes, and wherein at least one of the orthotic shells has a shape that closely matches the analysis to require minimal modification to match the analysis.

17. The system of claim 15, wherein the analysis obtains information concerning the patient's center of balance, which comprises, at least in part, a weighted average of a grid coordinate of data points weighted according pressure exerted on respective electrode cells by the patient's foot.

18. The system of claim 15, wherein the reader comprises a plurality of electrode cells comprising piezoelectric materials.

19. The system of claim 18, further comprising conductive foam in contact with the electrode cells.

* * * * *

UNITED STATES PATENT AND TRADEMARK OFFICE
CERTIFICATE OF CORRECTION

| | |
|---|---|
| PATENT NO. | : 8,036,768 B2 |
| APPLICATION NO. | : 11/877366 |
| DATED | : October 11, 2011 |
| INVENTOR(S) | : Craig E. Lowe |

It is certified that error appears in the above-identified patent and that said Letters Patent is hereby corrected as shown below:

In drawing, figure 6, in Reference Numeral 82, line 1, delete "D/A" and insert -- A/D --, therefor.

In column 5, line 11, delete "eletroconductive" and insert -- electroconductive --, therefor.

In column 10, line 51, after "the" insert -- 15 --.

In column 11, line 54, in Claim 1, delete "information:" and insert -- information; --, therefor.

In column 12, lines 23-24, in Claim 5, delete "info a on" and insert -- information --, therefor.

Signed and Sealed this
Twenty-ninth Day of May, 2012

David J. Kappos
*Director of the United States Patent and Trademark Office*